(12) United States Patent  
Hamilton et al.

(10) Patent No.: US 6,500,959 B1
(45) Date of Patent: Dec. 31, 2002

(54) PYRROLIDINE DERIVATIVES AND PROCESSES FOR PREPARING SAME

(75) Inventors: Gregory S. Hamilton, Catonsville; Joseph P. Steiner, Hampstead, both of MD (US)

(73) Assignee: GPI NIL Holdings, Inc., Wilmington, DE (US)

( * ) Notice: Subject to any disclaimer, the term of this patent is extended or adjusted under 35 U.S.C. 154(b) by 0 days.

(21) Appl. No.: 09/605,475

(22) Filed: Jun. 28, 2000

Related U.S. Application Data

(63) Continuation of application No. 08/833,629, filed on Apr. 8, 1997, which is a continuation of application No. 08/650,461, filed on May 21, 1996, now Pat. No. 5,859,031, which is a continuation-in-part of application No. 08/479,436, filed on Jun. 7, 1995, now Pat. No. 5,614,547.

(51) Int. Cl.$^7$ .............................................. C07D 207/16

(52) U.S. Cl. ........................................................ 548/533

(58) Field of Search ........................................ 548/533

(56) References Cited

U.S. PATENT DOCUMENTS

| | | | |
|---|---|---|---|
| 3,795,738 A | 3/1974 | Plotnikoff | |
| 3,810,884 A | 5/1974 | Gold | |
| 3,917,840 A | 11/1975 | Gold | |
| 4,070,361 A | 1/1978 | Petrillo, Jr. | |
| 4,128,653 A | 12/1978 | Cushman et al. | |
| 4,321,269 A | 3/1982 | Wareing | |
| 4,501,901 A | 2/1985 | Thottathil et al. | |
| 4,507,292 A | 3/1985 | Heywang et al. | |
| 4,604,402 A | 8/1986 | Godfrey, Jr. et al. | |
| 4,649,147 A | 3/1987 | Mueller et al. | |
| 4,708,954 A | 11/1987 | Ienaga et al. | |
| 4,762,821 A | 8/1988 | Nestor | |
| 4,912,231 A | 3/1990 | Kronenthal et al. | |
| 5,192,773 A | 3/1993 | Armistead et al. | |
| 5,204,338 A | 4/1993 | Baader et al. | |
| 5,330,993 A | 7/1994 | Armistead et al. | |
| 5,516,797 A | 5/1996 | Armistead et al. | |
| 5,589,499 A | 12/1996 | Weth | |
| 5,614,547 A | 3/1997 | Hamilton et al. | |
| 5,620,971 A | 4/1997 | Armistead et al. | |
| 5,622,970 A | 4/1997 | Armistead et al. | |
| 5,661,167 A | 8/1997 | Peet et al. | |
| 5,696,135 A | 12/1997 | Steiner et al. | |
| 5,721,256 A | 2/1998 | Hamilton et al. | |
| 5,726,184 A | 3/1998 | Zelle | |
| 5,780,484 A | 7/1998 | Zelle et al. | |
| 5,786,378 A | 7/1998 | Hamilton et al. | |
| 5,795,908 A | 8/1998 | Hamilton et al. | |
| 5,798,355 A | 8/1998 | Steiner et al. | |
| 5,801,187 A | 9/1998 | Li et al. | |
| 5,801,197 A | 9/1998 | Steiner et al. | |
| 5,811,434 A | 9/1998 | Zelle et al. | |
| 5,840,736 A | 11/1998 | Zelle et al. | |
| 6,037,370 A | 3/2000 | Armistead | |
| 6,124,328 A | 9/2000 | Armistead | |

OTHER PUBLICATIONS

US 5,654,332, 8/1997, Armistead (withdrawn)

Gold, B. et al., "Regulation of aberrant neurofilament phosporylation in neuronal perikarya. IV. Evidence for the involvement of two signals," *Brain Research*, 626 (1993) 23–30.

Dumont, F.J. "The Immunosuppressive and Toxic Effects of FK–506 are Mechanistically Related: Pharmacology of a Novel Antagonist of FK–506 and Rapamycin," *J. Exp. Med.*, 176 (1992) 751–60.

(List continued on next page.)

*Primary Examiner*—Robert Gerstl
(74) *Attorney, Agent, or Firm*—Lyon & Lyon LLP

(57) ABSTRACT

This invention relates to neurotrophic N-glyoxyl-prolyl ester compounds having an affinity for FKBP-type immunophilins, their preparation and use as inhibitors of the enzyme activity associated with immunophilin proteins, and particularly inhibitors of peptidyl-prolyl isomerase or rotamase enzyme activity.

4 Claims, 8 Drawing Sheets-

OTHER PUBLICATIONS

Schreiber, S.L. "Chemistry and Biology of the Immunophilins and Their Immunosuppressive Ligands," *Science*, 251 (1991) 283–87.

Jasperse, C. et al., "Sequential Radical Cyclization Approach to Propellane Triquinases. Total Synthesis of (±) –Modhephene," *J. Am. Chem. Soc.*, 112 (1990) 5601.

Iwabuchi, T. et al. "Effects of immunosuppressive peptidyl–propyl cis–trans isomerase (PPIase) inhibitors, cyclosporin A, FK506, ascomycin and rapamycin, on hair growth initiation in mouse: immunosuppression is not required for new hair growth," *J. of Dermatol. Sci.*, (1995) 9:1, 64–69.

Jiang, H. et al. "Induction of Anagen in Telogen Mouse Skin by Topical Application of FK506, a Potent Immunosuppressant," *J. Invest. Dermatol.*, (1995) 104:4, 523–525.

Yamamoto, Satoshi et al. "Stimulation of Hair Growth by Topical Application of FK506, a Potent Immunosuppressive Agent," *J. Invest. Dermatol.*, (1994) 102:2, 160–64.

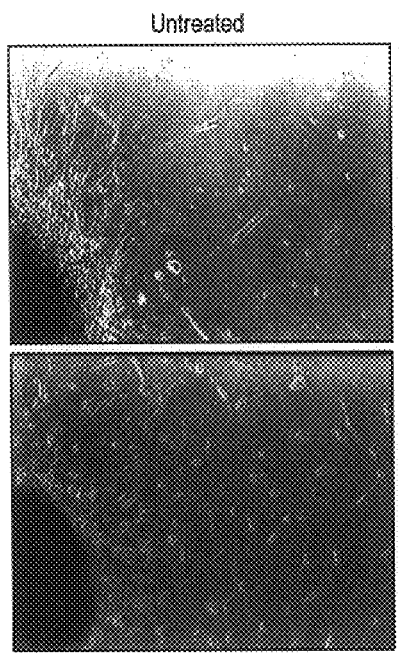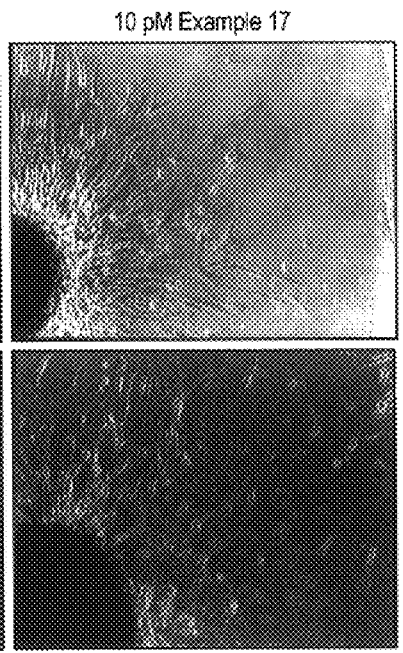

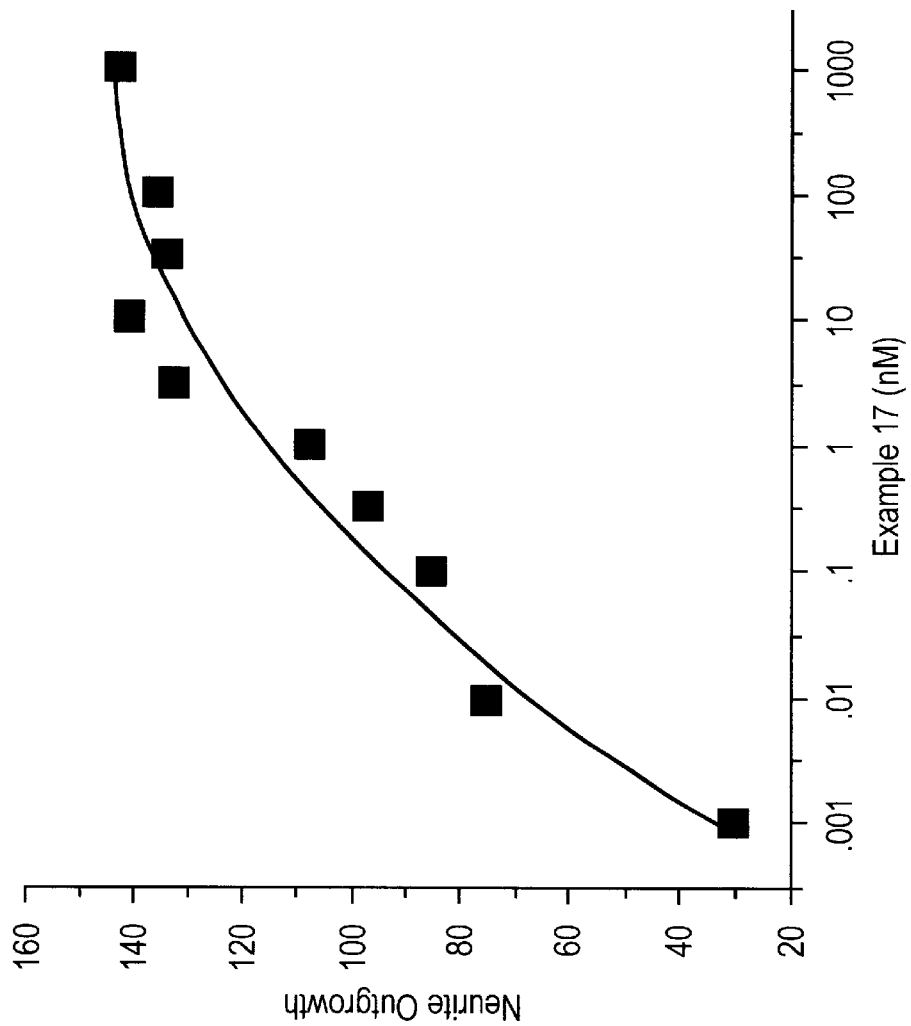

FIG. 3A
Sham
FIG. 3B
Vehicle
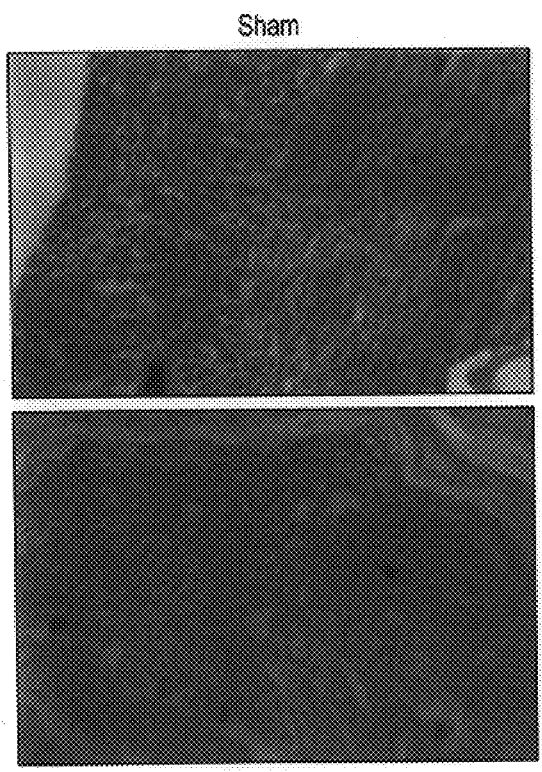
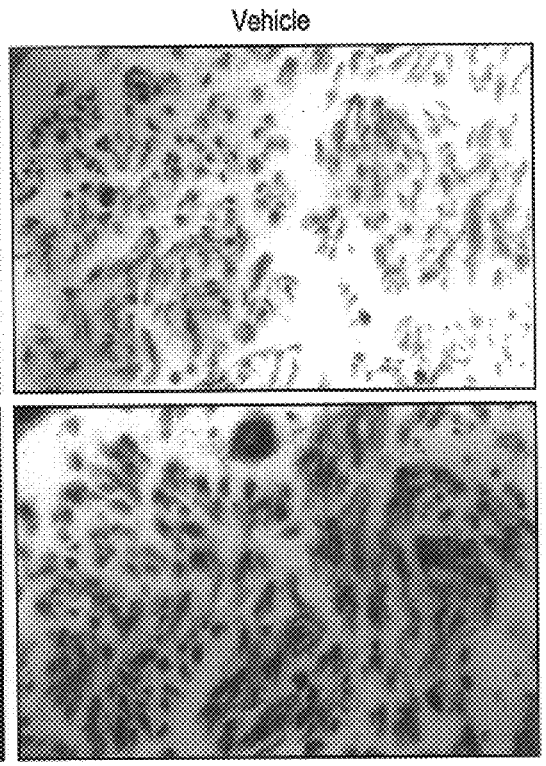
Example 1
FIG. 3C
Inactive
FIG. 3D

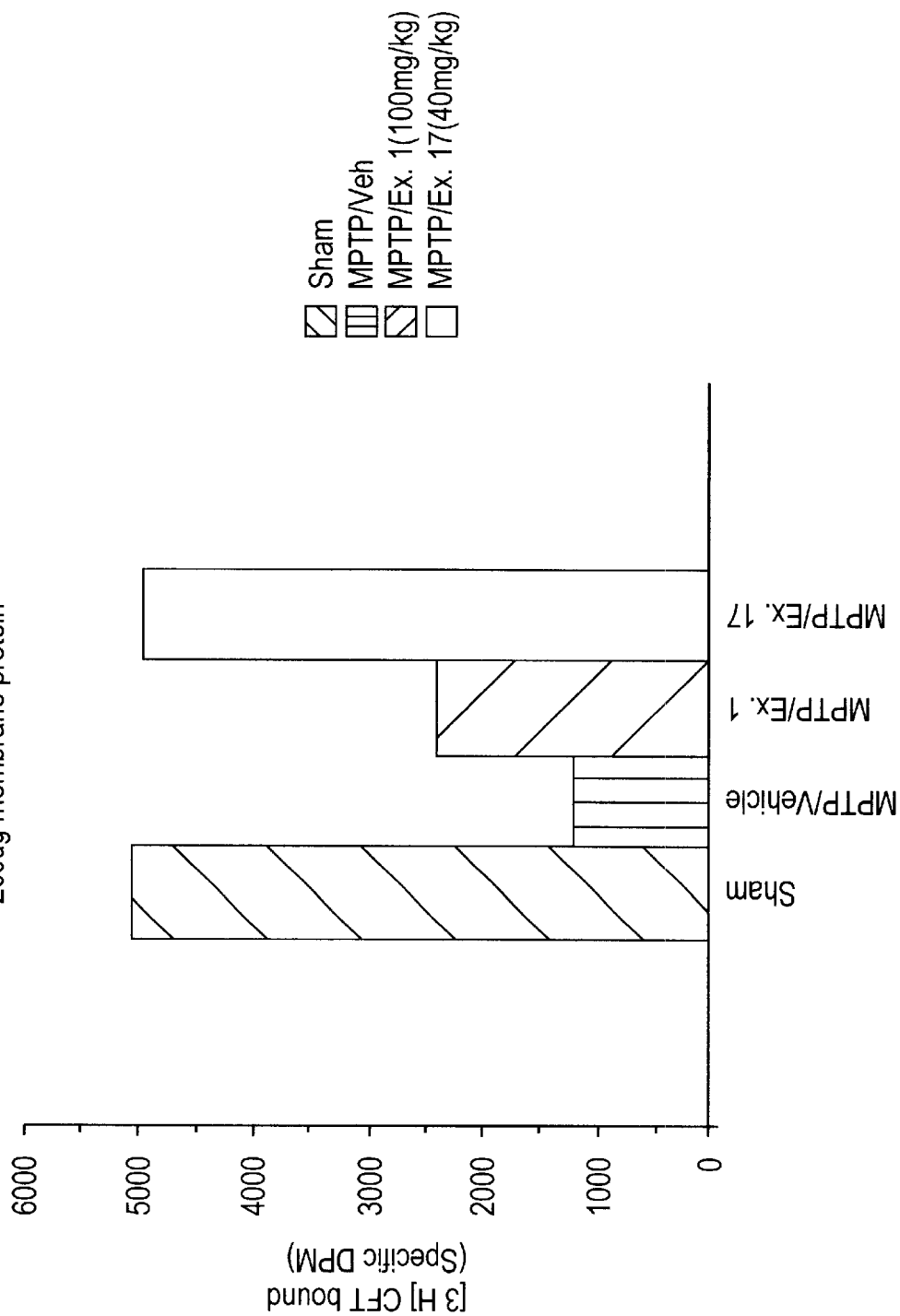

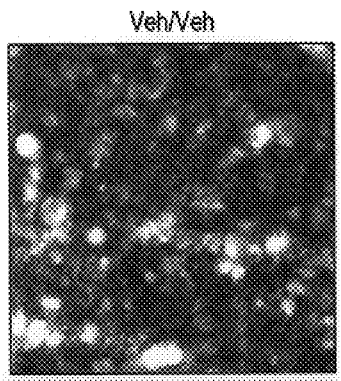
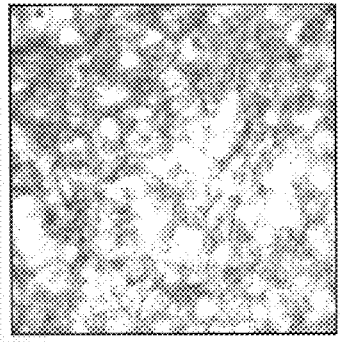
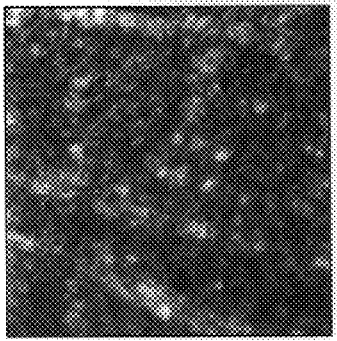
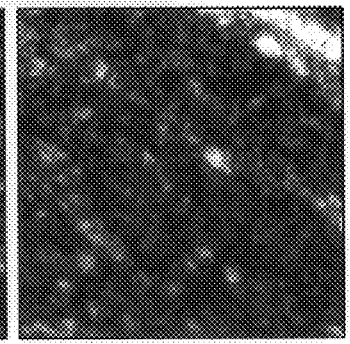
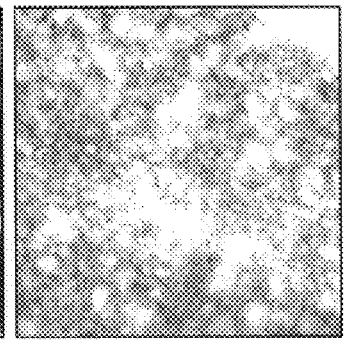
FIG. 6A  Veh/Veh
FIG. 6B  MPTP/Veh
FIG. 6C  MPTP/40 mg/kg Example 17
FIG. 6D  MPTP/20 mg/kg Example 17
FIG. 6E  MPTP/10 mg/kg Example 17
630X

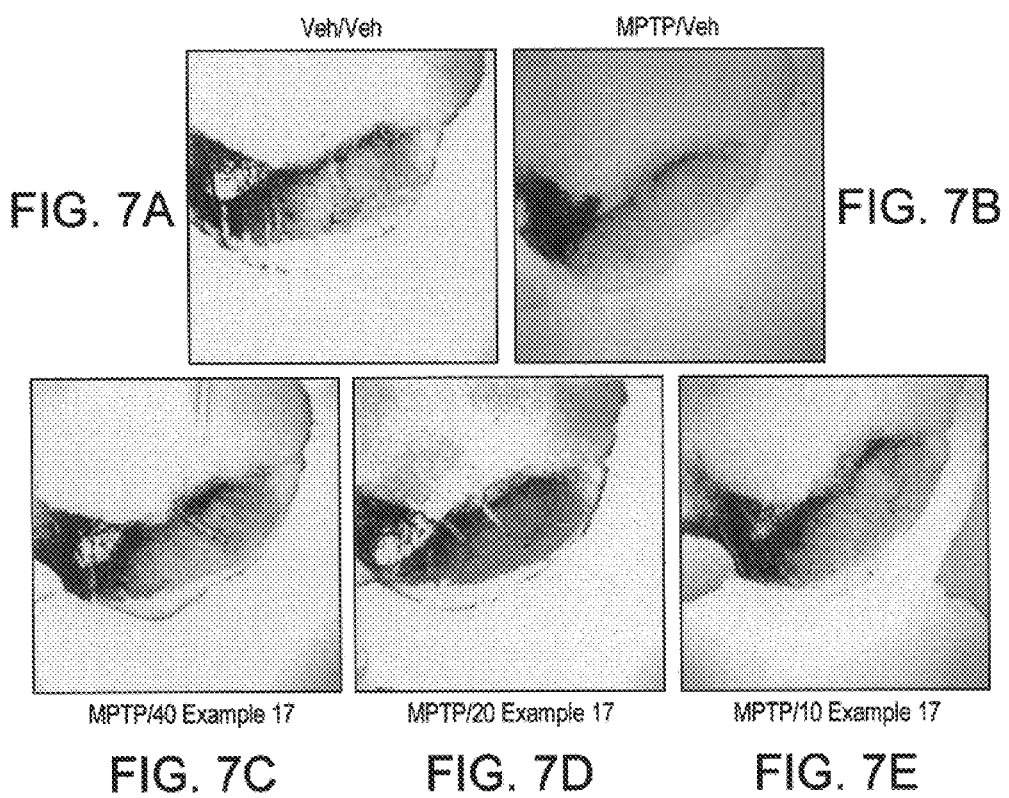
FIG. 7A Veh/Veh
FIG. 7B MPTP/Veh
FIG. 7C MPTP/40 Example 17
FIG. 7D MPTP/20 Example 17
FIG. 7E MPTP/10 Example 17
50X

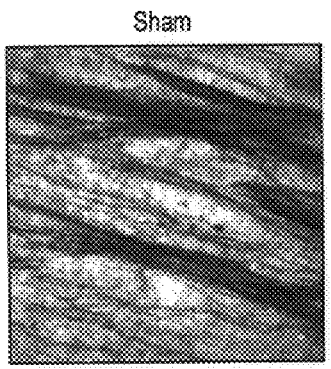
Sham
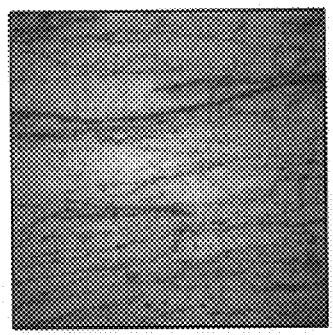
MPTP/Veh
FIG. 8A
FIG. 8B
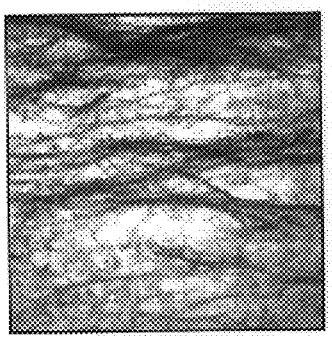
MPTP/40 Example 17
MPTP/20 Example 17
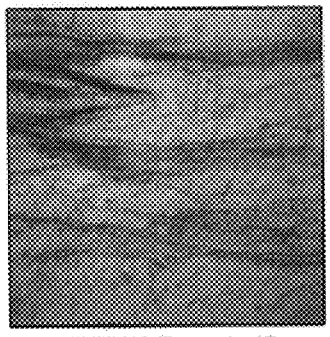
MPTP/10 Example 17
FIG. 8C
FIG. 8D
FIG. 8E
400X

PYRROLIDINE DERIVATIVES AND PROCESSES FOR PREPARING SAME

RELATED APPLICATION

This application is a Continuation of U.S. Pat. application Ser. No. 08/833,629, filed Apr. 8, 1997, which is a Continuation of U.S. Pat. application Ser. No. 08/650,461, filed May 21, 1996, granted as U.S. Pat. No. 5,859,031 on Jan. 12, 1999, which is a Continuation-in-Part of U.S. Pat. application Ser. No. 08/479,436, filed Jun. 7, 1995, granted as U.S. Pat. No. 5,614,547 on Mar. 25, 1997.

BACKGROUND OF THE INVENTION

1. Field of the Invention

This invention relates to neurotrophic compounds having an affinity for FKBP-type immunophilins, their preparation and use as inhibitors of the enzyme activity associated with immunophilin proteins, and particularly inhibitors of peptidyl-prolyl isomerase or rotamase enzyme activity.

2. Description of the Prior Art

The term immunophilin refers to a number of proteins that serve as receptors for the principal immunosuppressant drugs, cyclosporin A (CsA), FK506, and rapamycin. Known classes of immunophilins are cyclophilins, and FK506 binding proteins, such as FKBP. Cyclosporin A binds to cyclophilin while FK506 and rapamycin bind to FKBP. These immunophilin-drug complexes interface with a variety of intracellular signal transduction systems, especially in the immune system and the nervous system.

Immunophilins are known to have peptidyl-prolyl isomerase (PPIase) or rotamase enzyme activity. It has been determined that rotamase activity has a role in the catalyzation of the interconversion of the cis and trans isomer of immunophilin proteins.

Immunophilins were originally discovered and studied in immune tissue. It was initially postulated by those skilled in the art that inhibition of the immunophilins rotamase activity leads to the inhibition of T-cell proliferation, thereby causing the immunosuppressive action exhibited by immunosuppressive drugs such as cyclosporin A, KF506, and rapamycin. Further study has shown that the inhibition of rotamase activity, in and of itself, is not sufficient for immunosuppressant activity. Schreiber et al., *Science*, 1990 vol. 250 pp. 556–559. It has been shown that the immunophilin-drug complexes interact with ternary protein targets as their mode of action. Schreiber et al., *Cell*, 1991, vol. 66, pp. 807–815. In the case of FKBP-FK506 and FKBP-CsA, the drug-immunophilin complexes bind to the enzyme calcineurin, inhibitory T-cell receptor signalling leading to T-cell proliferation. Similarly, the complex of rapamycin and FKBP interacts with the RAFT1/FRAP protein and inhibits signalling from the IL-2 receptor.

Immunophilins have been found to be present at high concentrations in the central nervous system. Immunophilins are enriched 10–50 times more in the central nervous system than in the immune system. Within neural tissues, immunophilins appear to influence neutronal process extension, nitric oxide synthesis, and neurotransmitter release.

It has been found that picomolar concentrations of an immunosuppressant such as KF506 and rapamycin stimulate neurite out growth in PC12 cells and sensory nervous, namely dorsal root ganglion cells (DRGs). Lyons et al., *Proc. of Natl. Acad. Sci.*, 1994 vol. 91, pp. 3191–3195. In whole animal experiments, FK506 has been shown to stimulate nerve regeneration following facial nerve injury and results in functional recovery in animals with sciatic nerve lesions.

Surprisingly, it has been found that drugs with a high affinity for FKBP are potent rotamase inhibitors causing a neurotrophic effect. Lyons et al. These findings suggest the use of immunosuppressants in treating various peripheral neuropathies and enhancing neuronal regrowth in the central nervous system. (CNS). Studies have demonstrated that neurodegenerative disorders such as Alzheimer's disease, Parkinson's disease, and amyotrophic lateral sclerosis (ALS) may occur due to the loss, or decreased availability, of a neurotrophic substance specific for a particular population of neurons affected in the disorder.

Several neurotrophic factors effecting specific neuronal populations in the central nervous system have been identified. For example, it has been hypothesized that Alzheimer's disease results from a decrease or loss of nerve growth factor (NGF). It has thus been proposed to treat Alzheimer's patients with exogenous nerve growth factor or other neurotrophic proteins such as brain derived nerve factor (BDNF), glial derived nerve factor, ciliary neurotrophic factor, and neurotropin-3 to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressants exhibit a number of potentially serious side effects including nephrotoxicity, such as impairment of glomerular filtration and irreversible interstitial fibrosis (Kopp et al., 1991, *J. Am. Soc. Nephrol.* 1:162); neurological deficits, such as involuntary tremors, or non-specific cerebral angina such as non-localized headaches (De Groen et al., 1987, *N. Engl. J. Med.* 317:861); and vascular hypertension with complications resulting therefrom (Kahan et al., 1989 *N. Engl. J. Med.* 321: 1725).

In order to prevent the side effects associated with use of the immunosuppressant compounds, the present invention provides non-immunosuppressive compounds containing small molecule FKBP rotamase inhibitors for promoting neuronal growth and regeneration in various neuropathological situations where neuronal repair can be facilitated including peripheral nerve damage by physical injury or disease state such as diabetes, physical damage to the central nervous system (spinal cord and brain) brain damage associated with stroke, and for the treatment of neurological disorders relating to neurodegeneration, including Parkinson's disease, Alzheimer's disease, and amyotrophic lateral sclerosis.

SUMMARY OF THE INVENTION

The present invention relates to a novel class of neurotrophic compounds having an affinity for FKBP-type immunophilins. Once bound to this protein the neurotrophic compounds are potent inhibitors of the enzyme activity associated with immunophilin proteins and particularly rotamase enzyme activity, thereby stimulating neuronal regeneration and outgrowth. A key feature of the compounds of the present invention is that they do not exert any significant immunosuppressive activity in addition to their neurotrophic activity.

A preferred embodiment of this invention is a neurotrophic compound of the formula:

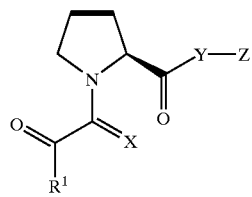

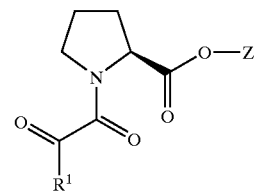

where

R$_1$ is selected from the group consisting of a C$_1$–C$_9$ straight or branched chain alkyl or alkenyl group optionally substituted with C$_3$–C$_8$ cycloalkyl, C$_3$ or C$_5$ cycloalkyl, C$_5$–C$_7$ cycloalkenyl, Ar$_1$, where said alkyl, alkenyl, cycloalkyl or cycloalkenyl groups may be optionally substituted with C$_1$–C$_4$ alkyl, C$_1$–C$_4$ alkenyl, or hydroxy, where Ar$_1$ is selected from the group consisting of 1-napthyl, 2-napthyl, 2-indolyl, 3-indolyl, 2-furyl, 3-furyl, 2-thiazolyl, 2-thienyl, 3-thienyl, 2-, 3-, 4-pyridyl, and phenyl, having one to three substituents which are independently selected from the group consisting of hydrogen, halo, hydroxyl, nitro, trifuloromethyl, C$_1$–C$_5$ straight or branched alkyl or alkenyl, C$_1$–C$_4$ alkoxy or C$_1$–C$_4$ alkenyloxy, phenoxy, benzyloxy, and amino;

X is selected from the group consisting of oxygen, sulfur, methylene (CH$_2$), or H$_2$;

Y is selected from the group consisting of oxygen or NR$_2$, where R$_2$ is hydrogen or C$_1$–C$_5$ alkyl; and Z is selected from the group consisting of C$_2$–C$_5$ straight or branched chain alkyl or alkenyl, wherein the alkyl chain is substituted in one or more positions with Ar$_1$ as defined above, C$_3$–C$_8$ cycloalkyl, cycloalkyl connected by a C$_1$–C$_5$ straight or unbranched alkyl or alkenyl chain, and Ar$_2$ where Ar$_2$ is selected from the group consisting of 2-indolyl, 3-indolyl, 2-furyl, 3-furyl, 2-thiazolyl, 2-thienyl, 3-thienyl, 2-, 3-, or 4-pyridyl, and phenyl, having one to three substituents which are independently selected from the group consisting of hydrogen, halo, hydroxyl, nitro, trifuloromethyl, C$_1$–C$_6$ straight or branched alkyl or alkenyl, C$_1$–C$_4$ alkoxy or C$_1$–C$_4$ alkenyloxy, phenoxy, benzyloxy, and amino; Z may also be the fragment:

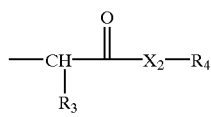

where

R$_3$ is selected from the group consisting of straight or branched alkyl C$_1$–C$_3$ optionally substituted with C$_3$–C$_5$ cycloalkyl, or Ar$_1$ as defined above, and unsubstituted Ar$_1$;

X$_2$ is O or NR$_5$, where R$_5$ is selected from the group consisting of hydrogen, C$_1$–C$_5$ straight or branched alkyl and alkenyl;

R$_4$ is selected from the group consisting of phenyl, benzyl, C$_1$–C$_5$ straight or branched alkyl or alkenyl, and C$_1$–C$_5$ straight or branched alkyl or alkenyl substituted with phenyl; or pharmaceutically acceptable salts or hydrates thereof.

Another preferred embodiment of this invention is a neurotrophic compound of the formula:

where

R$_1$ is a C$_1$–C$_9$ straight or branched chain alkyl or alkenyl group optionally substituted with C$_3$–C$_5$ cycloalkyl, C$_3$ or C$_5$ cycloalkyl, C$_5$–C$_7$ cycloalkenyl, or Ar$_1$, where said alkyl, alkenyl, cycloalkyl or cycloalkenyl groups may be optionally substituted with C$_1$–C$_4$ alkyl, C$_1$–C$_4$ alkenyl, or hydroxy, and where Ar$_1$ is selected from the group consisting of 1-napthyl, 2-napthyl, 2-indolyl, 3-indolyl, 2-furyl, 3-furyl, 2-thiazolyl, 2-thienyl, 3-thienyl, 2-, 3-, or 4-pyridyl, or phenyl, having one to three substituents which are independently selected from the group consisting of hydrogen, halo, hydroxyl, nitro, trifuloromethyl, C$_1$–C$_5$ straight or branched alkyl or alkenyl, C$_1$–C$_4$ alkoxy or C$_1$–C$_4$ alkenyloxy, phenoxy, benzyloxy, and amino;

Z is a C$_2$–C$_5$ straight or branched chain alkyl or alkenyl, wherein the alkyl chain is substituted in one or more positions with Ar$_1$ as defined above, C$_3$–C$_5$ cycloalkyl, cycloalkyl connected by a C$_1$–C$_5$ straight or unbranched alkyl or alkenyl chain, or Ar$_2$ where Ar$_2$ is selected from the group consisting of 2-indolyl, 3-indolyl, 2-furyl, 3-furyl, 2-thiazolyl, 2-thienyl, 3-thienyl, 2-, 3-, or 4-pyridyl, or phenyl, having one to three substituents which are independently selected from the group consisting of hydrogen, halo, hydroxyl, nitro, trifuloromethyl, C$_1$–C$_5$ straight or branched alkyl or alkenyl, C$_1$–C$_4$ alkoxy or C$_1$–C$_4$ alkenyloxy, phenoxy, benzyloxy, and amino; or pharmaceutically acceptable salts or hydrates thereof.

Another preferred embodiment of the invention is a neurotrophic compound having an affinity for FKBP-type immunophilins which inhibit the rotamase activity of the immunophilin.

Another preferred embodiment of the present invention is a method for treating a neurological disorder in an animal comprising administering a therapeutically effective amount of a compound having an affinity for FKBP-type immunophilins which inhibits the rotamase activity of the immunophilin.

Another preferred embodiment of the invention is a method of promoting neuronal regeneration and growth in mammals, comprising administering to a mammal an effective amount of a neurotrophic compound having an affinity for FKBP-type immunophilins which inhibits the rotamase activity of the immunophilin.

Yet another preferred embodiment of the invention is a method of preventing neurodegeneration in an animal comprising administering to an animal an effective amount of a neurotrophic compound having an affinity for FKBP-type immunophilins which inhibits rotamase activity of the immunophilin.

Another preferred embodiment is a neurotrophic N-glyoxyl prolyl ester compound of the formula:

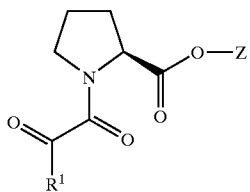

where
R$_1$ is a C$_1$–C$_5$ straight or branched chain alkyl or alkenyl group optionally substituted with C$_3$ to C$_6$ cycloalkyl, or Ar$_1$, where Ar$_1$ is selected from the group consisting of 2-furyl, 2-thienyl, or phenyl;

X is selected from the group consisting of oxygen and sulfur;

Y is oxygen; and

Z is a straight or branched chain alkyl or alkenyl, wherein the alkyl chain is substituted in one or more positions with Ar$_1$ as defined above, C$_3$–C$_6$ cycloalkyl, Ar$_2$ where Ar$_2$ is selected from the group consisting of 2-, 3-, or 4-pyridyl, or phenyl, having one to three substituents which are independently selected from the group consisting of hydrogen and C$_1$–C$_4$ alkoxy.

Particularly preferred neurotrophic N-glyoxyl prolyl ester compounds according to the above formula are selected from the group consisting of:

3-(2,5-dimethoxyphenyl)-1-propyl (2S)-1-(3,3-dimethyl-1,2-dioxopentyl)-2-pyrrolidinecarboxylate, 3-(2,5-dimethoxyphenyl)-1-prop-2-(E)-enyl (2S)1-(3,3-dimethyl-1,2-dioxopentyl)-2-pyrrolidine-carboxylate.

2-(3,4,5-trimethoxyphenyl)-1-ethyl (2S)-1-(3,3-dimethyl-1,2-dioxopentyl)-2-pyrrolidinecarboxylate, 3-(3-Pyridyl)-1-propyl (2S)-1-(3,3-dimethyl-1,2-dioxopentyl)-2-pyrrolidinecarboxylate, 3-(2-Pyridyl)-1-propyl (2S)-1-(3,3-dimethyl-1,2-dioxopentyl)-2-pyrrolidinecarobxylate, 3-(4-Pyridyl)-1-propyl (2S)-1-(3,3-dimethyl-1,2-dioxopentyl)-2-pyrrolidinecarboxylate, 3-phenyl-1-propyl (2S)-1-(2-tert-butyl-1,2-dioxoethyl)-2-pyrrolidinecarboxylate, 3-phenyl-1-propyl (2S)-1-(2-cyclohexylethyl-1,2-dioxoethyl)-2-pyrrolidinecarobxylate, 3-(3-pyridyl)-1-propyl (2S)-1-(2-cyclohexylethyl-1,2-dioxoethyl)-2-pyrrolidinecarboxylate, 3-(3-pyridyl)-1-propyl (2S)-1-(2-tert-butyl-1,2-dioxoethyl)-2-pyrrolidinecarboxylate, 3,3-diphenyl-1-propyl (2S)-1-(3,3-dimethyl-1,2-dioxopentyl)-2-pyrrolidinecarobxylate, 3-(3-pyridyl)-1-propyl (2S)-1-(2-cyclohexyl-1,2-dioxcethyl)-2-pyrrolidinecarboxylate, 3-(3-Pyridyl)-1-propyl (2S)-N-([2-thienyl] glyoxyl) pyrrolidinecarboxylate, 3,3-Diphenyl-1-propyl (2S)-1-(3,3-dimethyl-1,2-dioxobutyl)-2-pyrrolidinecarboxylate, 3,3-Diphenyl-1-propyl (2S)-1-cyclohexylglyoxyl-2-pyrrolidinecarboxylate, and 3,3-Diphenyl-1-propyl (2S)-1-(2-thienyl)glyoxyl-2-pyrrolidinecarboxylate.

BRIEF DESCRIPTION OF THE DRAWINGS

FIGS. 1A–1D are photomicrographs of chick dorsal root ganglia treated with various concentrations of Example 17 as indicated. FIGS. 1A–1D show that Example 17 of the present invention potently promotes neurite outgrowth in sensory neuronal cultures. Explant cultures isolated form embryonic day 9–10 chick dorsal root ganglia were treated with various concentrations of Example 17 as indicated. Forty-eight hours later, the number of neurite with a length greater than one DRG explant was quantitated. The number of neurites expressed in untreated DRG's was subtracted from the neurite number of Example 17—treated samples to yield Example 17—dependent specific neurite outgrowth. Micrographs of Example 17-treated DRG's, as well as quantitative dose-dependent neurite outgrowth elicited by Example 17 are presented.

FIG. 2 is a graph showing quantitation of neurite outgrowth in chick dorsal root ganglia treated with various concentrations of Example 17 as indicated. FIG. 2 shows that Example 17 of the present invention potently promotes neurite outgrowth in sensory neuronal cultures. Explant cultures isolated form embryonic day 9–10 chick dorsal root ganglia were treated with various concentrations of Example 17 as indicated. Forty-eight hours later, the number of neurite with a length greater than one DRG explant was quantitated. The number of neurites expressed in untreated DRG's was subtracted form the neurite number of Example 17—treated samples to yield Example 17—dependent specific neurite outgrowth. Quantitative dose-dependent neurite outgrowth elicited by Example 17 is presented.

FIGS. 3A–3D are photomicrographs of rat scriatic nerve sections. FIGS. 3A–3D show that Example 1 of the present invention promotes neuronal regeneration following sciatic nerve lesions. Sciatic nerves of 150 g male Sprague-Dawley rats were crushed at the level of the hips. Example 1 (30 mg/kg s.c.), Inactive (30 mg/kg s.c.) or intralipid vehicle was administered once daily for the next 21 days. Animals were sacrificed, sciatic nerves removed and nerve segments 2 mm distal to the crush site were sectioned and stained with Holmes silver stain (to assess axon number) and Luxol fast blue (to assess remyelination). The micrographs show sciatic nerve sections of sham operated rats, vehicle-treated lesioned animals. Example 1-treated and inactive-treated animals at 630x magnification, four animals per group.

FIG. 4 shows that neuroimmunophilin ligands of the present invention promote recovery of dopamine neurons following MPTP treatment of mice. CD1 mice (25 g) were treated daily with 30 mg/kg MPTP (i.p.) for 5 days. The animals were also treated daily with intralipid vehicle, Example 1 (100 mg/kg s.c.) or Example 17 (40, 20, 10 mg/kg s.c., as indicated) concurrently with the MPTP and continued for an additional 5 days. After eighteen days, the mice were sacrificed, striata from 5 animals per group were pooled and processed into a washed membrane preparation. Binding of [3H]-CFT to these striated membrane preparations of various groups was quantitated to determine dopamine transporter levels on viable nerve terminals. Binding in the presence of 10 $\mu$M unlabelled CFT provided on estimate of nonspecific binding, which as subtracted from the total binding to quantitative specific [3H]-CFT bound. Binding was normalized to the protein content of the striatal membranes from each experimental group. Coronal and saggital brain sections from MPTP and drug treated animals were stained with anti-tyrosine hydroxylase (TH) Ig to quantitate striatal, medial forebrain bundle axonal and nigral levels of TH, which is indicative of functional dopaminergic neurons.

FIG. 5 is a bar graph of [$^3$H]-CFT plotted for 200 $\mu$g of membrane protein. FIG. 5 shows that neuroimmunophilin ligands of the present invention promote recovery of dopamine neurons following MPTP treatment of mice in accordance with the procedure described in FIG. 4.

FIGS. 6A–6E are photomicrographs, at 630x magnification, of coronal and saggital brain sections. FIGS.

Figure 4:
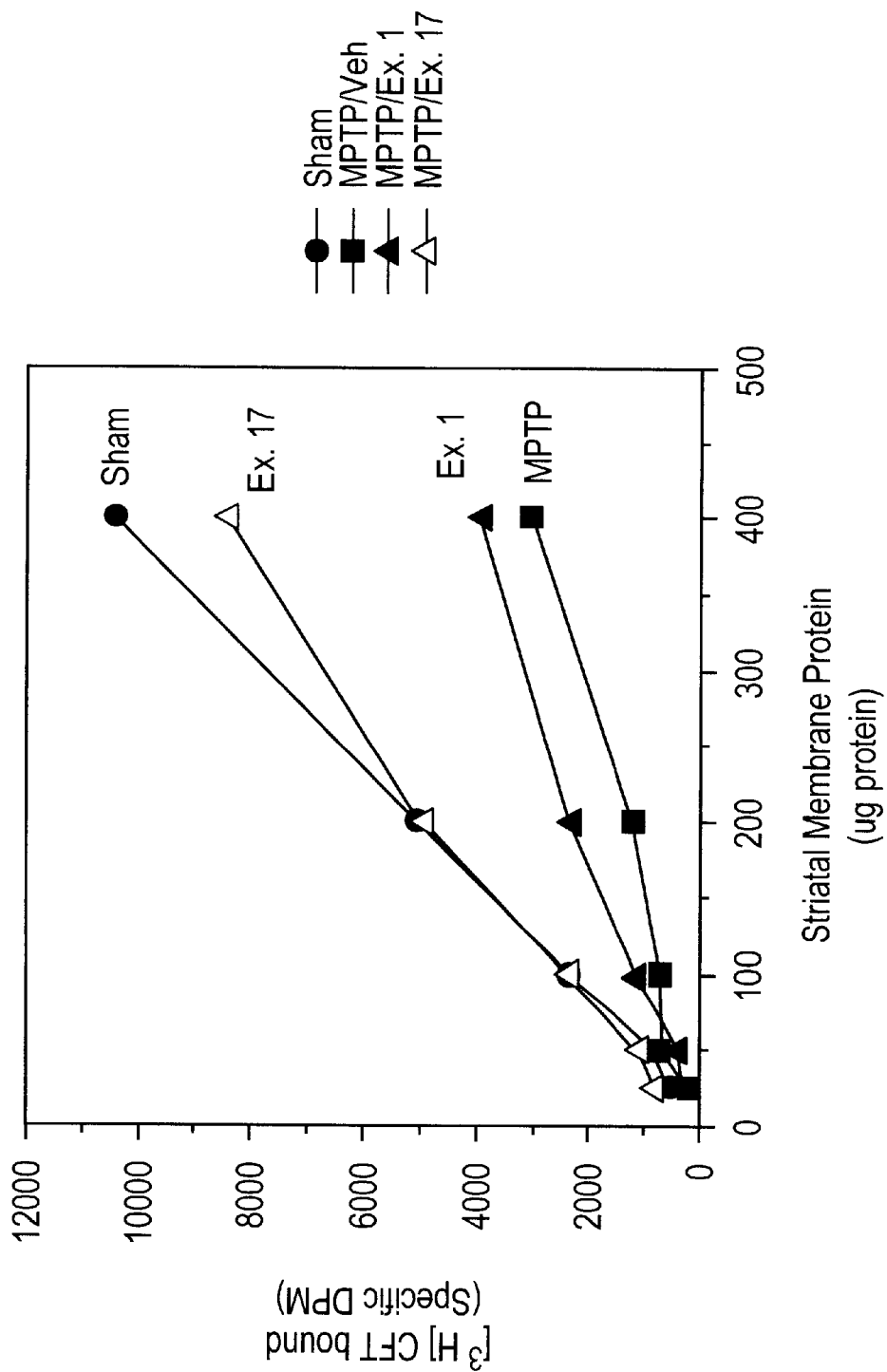
FIG. 4 is a graph of [$^3$H]-CFT binding per $\mu$g of Striatal Membrane Protein.

6A–6E show brain sections from MPTP and drug treated animals stained with anti-tyrosine hydroxylase (TH) Ig to quantitate striatal levels of TH, which is indicative of functional dopaminergic neurons.

FIGS. 7A–7E are photomicrographs, at 50x magnification, of coronal and saggital brain sections. FIGS. 7A–7E show brain sections from MPTP and drug treated animals stained with anti-tyrosine hydroxylase (TH) Ig to quantitate nigral levels of TH, which is indicative of functional dopaminergic neurons.

FIGS. 8A–8E are photomicrographs, at 400x magnification, of coronal and saggital brain sections. FIGS. 8A–8E show brain sections from MPTP and drug treated animals stained with anti-tyrosine hydroxylase (TH) Ig to quantitate medial forebrain bundle axonal levels of TH, which is indicative of functional dopaminergic neurons.

DETAILED DESCRIPTION OF THE INVENTION

The novel neurotrophic compounds of this invention are relatively small molecules in relation to other known compounds which bind to FKBP-type immunophilins, such as rapamycin, FK506, and cyclosporin.

The neurotrophic compounds of this invention have an affinity for the FK506 binding proteins such as FKBP-12. When the neurotrophic compounds of the invention are bound to the FKBP, they have been found to unexpectedly inhibit the prolyl- peptidyl cis-trans isomerase activity, or rotamase activity of the binding protein and stimulate neurite growth, while not exhibiting an immunosuppressant effect.

More particularly, this invention relates to a novel class of neurotrophic compounds represented by the formula:

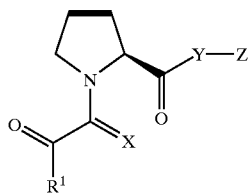

where
- $R_1$ is a $C_1$–$C_9$ straight or branched chain alkyl or alkenyl group optionally substituted with $C_3$–$C_8$ cycloalkyl, $C_3$ or $C_5$ cycloalkyl, $C_5$–$C_7$ cycloalkenyl, or $Ar_2$, where said alkyl, alkenyl, cycloalkyl or cycloalkenyl groups may be optionally substituted with $C_1$–$C_4$ alkyl, $C_1$–$C_4$ alkenyl, or hydroxy, and where $Ar_1$ is selected from the group consisting of 1-napthyl, 2-napthyl, 2-indolyl, 3-indolyl, 2-furyl, 3-furyl, 2-thiazolyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$–$C_5$ straight or branched alkyl or alkenyl, $C_1$–$C_4$ alkoxy or $C_1$–$C_4$ alkenyloxy, phenoxy, benzyloxy, and amino;
- X is oxygen, sulfur, methylene ($CH_2$), or $H_2$;
- Y is oxygen or $NR_2$, where $R_2$ is hydrogen or $C_1$–$C_6$ alkyl; and
- Z is a $C_2$–$C_6$ straight or branched chain alkyl or alkenyl, wherein the alkyl chain is substituted in one or more positions with $Ar_1$ as defined above, $C_3$–$C_5$ cycloalkyl, cycloalkyl connected by a $C_1$–$C_5$ straight or unbranched alkyl or alkenyl chain, or $Ar_2$ where $Ar_2$ is selected from the group consisting of 2-indolyl, 3-indolyl, 2-furyl, 3-furyl, 2-thiazolyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$–$C_5$ straight or branched alkyl or alkenyl, $C_1$–$C_4$ alkoxy or C1–C4 alkenyloxy, phenoxy, benzyloxy, and amino;

Z may also be the fragment:

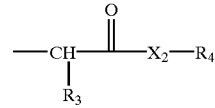

where
- $R_3$ is selected from the group consisting of straight or branched alkyl $C_1$–$C_5$ optionally substituted with $C_3$–$C_8$ cycloalkyl, or $Ar_1$ as defined above, and unsubstituted $Ar_1$;
- $X_2$ is O or $NR_5$, where $R_5$ is selected from the group consisting of hydrogen, $C_1$–$C_6$ straight or branched alkyl and alkenyl;
- $R_4$ is selected from the group consisting of phenyl, benzyl, $C_1$–$C_5$ straight or branched alkyl or alkenyl, and $C_1$–$C_5$ straight or branched alkyl or alkenyl substituted with phenyl; or pharmaceutically acceptable salts or hydrates thereof.

Preferred compounds have the following formula:

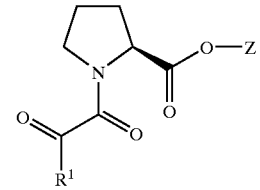

where
- $R_1$ is a $C_1$–$C_9$ straight or branched chain alkyl or alkenyl group optionally substituted with $C_3$–$C_8$ cycloalkyl, $C_3$ or $C_5$ cycloalkyl, $C_5$–$C_7$ cycloalkenyl, or $Ar_1$, where said alkyl, alkenyl, cycloalkyl or cycloalkenyl groups may be optionally substituted with $C_1$–$C_4$ alkyl, $C_1$–$C_4$ alkenyl, or hydroxy, and where $Ar_1$ is selected from the group consisting of 1-napthyl, 2-napthyl, 2-indolyl, 3-indolyl, 2-furyl, 3-furyl, 2-thiazolyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino;
- Z is a $C_2$–$C_6$ straight or branched chain alkyl or alkenyl, wherein the alkyl chain is substituted in one or more positions with $Ar_1$ as defined above, C3–C8 cycloalkyl, cycloalkyl connected by a $C_1$–$C_6$ straight or unbranched alkyl or alkenyl chain, or $Ar_2$ where $Ar_2$ is selected from the group consisting of 2-indolyl, 3-indolyl, 2-furyl, 3-furyl, 2-thiazolyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino; or pharmaceutically acceptable salts or hydrates thereof.

Preferred neurotrophic N-glyoxyl prolyl ester compounds have the formula:

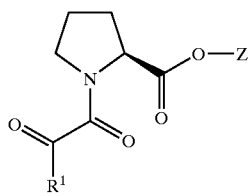

where
R$_1$ is a C$_1$–C$_5$ straight or branched chain alkyl or alkenyl group optionally substituted with C$_3$ to C$_6$ cycloalkyl, or Ar$_1$, where Ar$_1$ is selected from the group consisting of 2-furyl, 2-thienyl, or phenyl;

X is selected from the group consisting of oxygen and sulfur;

Y is oxygen; and

Z is a straight or branched chain alkyl or alkenyl, wherein the alkyl chain is substituted in one or more positions with Ar$_1$ as defined above, C$_3$–C$_6$ cycloalkyl, Ar$_2$ where Ar$_2$ is selected from the group consisting of 2-, 3-, or 4-pyridyl, or phenyl, having one to three substituents which are independently selected from the group consisting of hydrogen and C$_1$–C$_4$ alkoxy.

The compounds of this invention exist as stereoisomeric forms, either enantiomers or diastereoisomers. The stereochemistry at position 1 (Formula 1) is R or S, with S preferred. Included within the scope of the invention are the enantiomers, the racemic form, and diastereoisomeric mixtures. Enantiomers as well as diastereoisomers can be separated by methods known to those skilled in the art.

It is known that immunophilins such as FKBP preferentially recognize peptide substrates containing Xaa-Pro-Yaa motifs, where Xaa and Yaa are lipophilic amino acid residues. Schreiber et al. 1990 *J. Org. Chem.* 55, 4984–4986; Harrison and Stein, 1990 *Biochemistry*, 29, 3813–3816. Thus modified prolyl peptidomimetic compounds bearing lipophilic substituents should bind with high affinity to the hydrophobic core of the FKBP active site and inhibit its rotamase activity.

Preferred compounds of the present invention include R$_1$ groups which are not stereochemically bulky in relation to the known shape and size of the hydrophobic core of the FKBP active site. Thus, very large and/or highly substituted R$_1$ groups would bind with less affinity to the FKBP active site.

Preferred compounds of the invention include:
3-phenyl-1-propyl (2S)-1-(3,3-dimethyl-1,2-dioxopentyl)-2-pyrrolidinecarboxylate,
3-phenyl-1-prop-2-(E)-enyl (2S)-1-(3,3-dimethyl-1,2-dioxopentyl)-2-pyrrolidinecarboxylate,
3-(3,4,5-trimethoxyphenyl)-1-propyl (2S)-1-(3,3-dimethyl-1,2-dioxopentyl)-2-pyrrolidinecarboxylate,
3-(3,4,5-trimethoxyphenyl)-1-prop-2-(E)-enyl (2S)-1-(3,3-dimethyl-1,2-dioxopentyl)-2-pyrrolidine carboxylate,
3-(4,5-methylenedioxyphenyl)-1-propyl (2S)-1-(3,3-dimethyl-1,2-dioxopentyl)-2-pyrrolidinecarboxylate,
3-(4,5-methylenedioxyphenyl)-1-prop-2-(E)-enyl (2S)-1-(3,3-dimethyl-1,2-dioxopentyl)-2-pyrrolidinecarboxylate,
3-cyclohexyl-1-propyl (2S)-1-(3,3-dimethyl-1,2-dioxopentyl)-2-pyrrolidinecarboxylate,
3-cyclohexyl-1-prop-2-(E)-enyl (2S)-1-(3,3-dimethyl-1,2-dioxopentyl)-2-pyrrolidinecarboxylate,
(1R)-1,3-diphenyl-1-propyl (2S)-1-(3,3-dimethyl-1,2-dioxopentyl)-2-pyrrolidinecarboxylate,
3-phenyl-1-propyl (2S)-1-(1,2-dioxo-2-[2-furanyl])ethyl-2-pyrrolidinecarboxylate,
3-phenyl-1-propyl (2S)-1-(1,2-dioxo-2-[2-thienyl])ethyl-2-pyrrolidinecarboxylate,
3-phenyl-1-propyl (2S)-1-(1,2-dioxo-2-[2-thiazolyl])ethyl-2-pyrrolidinecarboxylate,
3-phenyl-1-propyl (2S)-1-(1,2-dioxo-2-phenyl)ethyl-2-pyrrolidinecarboxylate,
3-(2,5-dimethoxyphenyl)-1-propyl (2S)-1-(3,3-dimethyl-1,2-dioxopentyl)-2-pyrrolidinecarboxylate,
3-(2,5-dimethoxyphenyl)-1-prop-2-(E)-enyl (2S)-1-(3,3-dimethyl-1,2-dioxopentyl)-2-pyrrolidinecarboxylate,
2-(3,4,5-trimethoxyphenyl)-1-ethyl (2S)-1-(3,3-dimethyl-1,2-dioxopentyl)-2-pyrrolidinecarboxylate,
3-(3-Pyridyl)-1-propyl (2S)-1-(3,3-dimethyl-1,2-dioxopentyl)-2-pyrrolidinecarboxylate,
3-(2-Pyridyl)-1-propyl (2S)-1-(3,3-dimethyl-1,2-dioxopentyl)-2-pyrrolidinecarboxylate,
3-(4-Pyridyl)-1-propyl (2S)-1-(3,3-dimethyl-1,2-dioxopentyl)-2-pyrrolidinecarboxylate,
3-phenyl-1-propyl (2S)-1-(2-cyclohexyl-1,2-dioxoethyl)-2-pyrrolidinecarboxylate,
3-phenyl-1-propyl (2S)-1-(2-tert-butyl-1,2-dioxoethyl)-2-pyrrolidinecarboxylate,
3-phenyl-1-propyl (2S)-1-(2-cyclohexylethyl-1,2-dioxoethyl)-2-pyrrolidinecarboxylate,
3-(3-pyridyl)-1-propyl (2S)-1-(2-cyclohexylethyl-1,2-dioxoethyl)-2-pyrrolidinecarboxylate,
3-(3-pyridyl)-1-propyl (2S)-1-(2-tert-butyl-1,2-dioxoethyl)-2-pyrrolidinecarboxylate,
3,3-diphenyl-1-propyl (2S)-1-(3,3-dimethyl-1,2-dioxopentyl)-2-pyrrolidinecarboxylate,
3-(3-pyridyl)-1-propyl (2S)-1-(2-cyclohexyl-1,2-dioxoethyl)-2-pyrrolidinecarboxylate,
3-(3-Pyridyl)-1-propyl (2S)-N-([2-thienyl]glyoxyl) pyrrolidinecarboxylate,
3,3-Diphenyl-1-propyl (2S)-1-(3,3-dimethyl-1,2-dioxobutyl)-2-pyrrolidinecarboxylate,
3,3-Diphenyl-1-propyl (2S)-1-cyclohexylglyoxyl-2-pyrrolidinecarboxylate,
3,3-Diphenyl-1-propyl (2S)-1-(2-thienyl)glyoxyl-2-pyrrolidinecarboxylate.

Particularly preferred neurotrophic N-glyoxyl prolyl ester compounds are selected from the group consisting of:
3-(2,5-dimethoxyphenyl)-1-propyl (2S)-1-(3,3-dimethyl-1,2-dioxopentyl)-2-pyrrolidinecarboxylate,
3-(2,5-dimethoxyphenyl)-1-prop-2-(E)-enyl (2S)-1-(3,3-dimethyl-1,2-dioxopentyl)-2-pyrrolidinecarboxylate,
2-(3,4,5-trimethoxyphenyl)-1-ethyl (2S)-1-(3,3-dimethyl-1,2-dioxopentyl)-2-pyrrolidinecarboxylate,
3-(3-Pyridyl)-1-propyl (2S)-1-(3,3-dimethyl-1,2-dioxopentyl)-2-pyrrolidinecarboxylate,
3-(2-Pyridyl)-1-propyl (2S)-1-(3,3-dimethyl-1,2-dioxopentyl)-2-pyrrolidinecarboxylate,
3-(4-Pyridyl)-1-propyl (2S)-1-(3,3-dimethyl-1,2-dioxopentyl)-2-pyrrolidinecarboxylate,
3-phenyl-1-propyl (2S)-1-(2-tert-butyl-1,2-dioxoethyl)-2-pyrrolidinecarboxylate,
3-phenyl-1-propyl (2S)-1-(2-cyclohexylethyl-1,2-dioxoethyl)-2-pyrrolidinecarboxylate,
3-(3-pyridyl)-1-propyl (2S)-1-(2-cyclohexylethyl-1,2-dioxoethyl)-2-pyrrolidinecarboxylate,
3-(3-pyridyl)-1-propyl (2S)-1-(2-tert-butyl-1,2-dioxoethyl)-2-pyrrolidinecarboxylate,
3,3-diphenyl-1-propyl (2S)-1-(3,3-dimethyl-1,2-dioxopentyl)-2-pyrrolidinecarboxylate, 3-(3-pyridyl)-1-propyl (2S)-1-(2-cyclohexyl-1,2-dioxoethyl)-2-pyrrolidinecarboxylate, 3-(3-Pyridyl)-1-propyl (2S)-N-([2-thienyl]glyoxyl) pyrrolidinecarboxylate, 3,3-Diphenyl-1-propyl (2S)-1-(3,3-dimethyl-1,2-dioxobutyl)-2-pyrrolidinecarboxylate, 3,3-Diphenyl-1-propyl (2S)-1-cyclohexylglyoxyl-2-pyrrolidinecarboxylate, and 3,3-Diphenyl-1-propyl (2S)-1-(2-thienyl)glyoxyl-2-pyrrolidinecarboxylate.

The compounds of the present invention can be used in the form of salts derived from inorganic or organic acids and bases. Included among such acid salts are the following: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemissulfate heptanoate, hexanoate, hydrochloride, hydrobromide, hydroiodide, 2-hydroxyethanesulfonate, lactate, maleate, methanesulfonate, 2-naphthalensulfonate, nicotinate, oxalate, pamoate, pectinate, propionate, succinate, tartrate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The neurotrophic compounds of this invention can be periodically administered to a patient undergoing treatment for neurological disorders or for other reasons in which it is desirable to stimulate neuronal regeneration and growth, such as in various peripheral neuropathic and neurological disorders relating to neurodegeneration. The compounds of this invention can also be administered to mammals other than humans for treatment of various mammalian neurological disorders.

The novel compounds of the present invention are potent inhibitors of rotamase activity and possess an excellent degree of neurotrophic activity. This activity is useful in the stimulation of damaged neurons, the promotion of neuronal regeneration, the prevention of neurodegeneration, and in the treatment of several neurological disorders known to be associated with neuronal degeneration and peripheral neuropathies. The neurological disorders that may be treated include but are not limited to: trigeminal neuralgia, glossopharyngeal neuralgia, Bell's Palsy, myasthenia gravis, muscular dystrophy, amyotrophic lateral sclerosis, progressive muscular atrophy, progressive bulbar inherited muscular atrophy, herniated, ruptured or prolapsed invertabrae disk syndromes, cervical spondylosis, plexus disorders, thoracic outlet destruction syndromes, peripheral neuropathic such as those caused by lead, dapsone, ticks, prophyria, or Gullain-Barré syndrome, Alzheimer's disease, and Parkinson's disease.

For these purposes the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets the immunophilin-drug complex should readily penetrate the blood-brain barrier when peripherally administered. Compounds of this invention which cannot penetrate the blood-brain barrier can be effectively administered by an intraventricular route.

The pharmaceutical compositions may be in the form of a sterile injectable preparation, for example as a sterile injectable aqueous or oleaginous suspension. This suspension may be formulated according to techniques know in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. Fatty acids such as oleic acid and its glyceride derivatives find use in the preparation of injectables, olive oil or castor oil, especially in their polyoxyethylated versions. These oil solutions or suspensions may also contain a long-chain alcohol diluent or dispersant.

The compounds may be administered orally in the form of capsules or tablets, for example, or as an aqueous suspension or solution. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening and/or flavoring and/or coloring agents may be added.

The compounds of this invention may also be administered in the form of suppositories for rectal administration of the drug. These compositions can be prepared by mixing the drug with a suitable non-irritating excipient which is solid at room temperature but liquid at rectal temperature and therefore will melt in the rectum to release the drug. Such materials include cocoa butter, beeswax and polyethylene glycols.

The compounds of this invention may also be administered optically, especially when the conditions addressed for treatment involve areas or organs readily accessible by topical application, including neurological disorders of the eye, the skin, or the lower intestinal tract. Suitable topical formulations are readily prepared for each of these areas.

For ophthalmic use, the compounds can be formulated as micronized suspensions in isotonic, pH adjusted sterile saline, or, preferably, as solutions is isotonic, pH adjusted sterile saline, either with or without a preservative such as benzylalkonium chloride. Alternatively for the ophthalmic uses the compounds may be formulated in an ointment such as petrolatum.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see above) or in a suitable enema formulation.

Dosage levels on the order of about 0.1 mg to about 10,000 mg. of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

The compounds can be administered with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

$K_i$ Test Procedure

Inhibition of the peptidyl-prolyl isomerase (rotamase) activity of the inventive compounds can be evaluated by known methods described in the literature (Harding, M. W. et al. *Nature* 341: 758–760 (1989); Holt et al. *J. Am. Chem. Soc.* 115: 9923–9938). These values are obtained as apparent $K_i$'s and are presented in Table I. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $K_i$ values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 sec using a spectrophotometer and the rate constants are determined from the absorbance versus time data files.

The data for these experiments is presented in Table I.

TABLE I

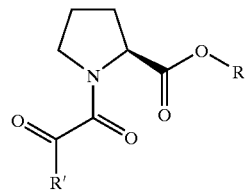

| No. | R | R' | $K_i$ |
|---|---|---|---|
| 1 | 1,1-dimethylpropyl | 3-phenylpropyl | 42 |
| 2 | " | 3-phenyl-prop-2-(E)-enyl | 125 |
| 3 | " | 3-(3,4,5-trimethoxyphenyl)propyl | 200 |
| 4 | " | 3-(3,4,5-trimethoxyphenyl)-prop-2-(E)-enyl | 65 |
| 5 | " | 3-(4,5-methylenedioxy)phenylpropyl | 170 |
| 6 | " | 3-(4,5-methylenedioxy)phenylprop-2-(E)-enyl | 160 |
| 7 | " | 3-cyclohexylpropyl | 200 |
| 8 | " | 3-cyclohexylprop-2-(E)-enyl | 600 |
| 9 | " | (1R)-1,3-diphenyl-1-propyl | 52 |
| 10 | 2-furanyl | 3-phenylpropyl | 4000 |
| 11 | 2-thienyl | " | 92 |
| 12 | 2-thiazolyl | " | 100 |
| 13 | phenyl | " | 1970 |
| 14 | 1,1-dimethylpropyl | 3-(2,5-dimethoxy)phenylpropyl | 250 |
| 15 | " | 3-(2,5-dimethoxy)phenylprop-2-(E)-enyl | 450 |
| 16 | " | 2-(3,4,5-trimethoxyphenyl)ethyl | 120 |
| 17 | " | 3-(3-pyridyl)propyl | 5 |
| 18 | " | 3-(2-pyridyl)propyl | 195 |
| 19 | " | 3-(4-pyridyl)propyl | 23 |
| 20 | cyclohexyl | 3-phenylpropyl | 82 |
| 21 | tert-butyl | " | 95 |
| 22 | cyclohexylethyl | " | 1025 |
| 23 | cyclohexylethyl | 3-(3-pyridyl)propyl | 1400 |
| 24 | tert-butyl | 3-(3-pyridyl)propyl | 3 |
| 25 | 1,1-dimethylpropyl | 3,3-diphenylpropyl | 5 |
| 26 | cyclohexyl | 3-(3-pyridyl)propyl | 9 |
| 27 | 2-thienyl | 3-(3-pyridyl)propyl | 1000 |
| 28 | tert-butyl | 3,3-diphenylpropyl | 5 |
| 29 | cyclohexyl | " | 20 |
| 30 | 2-thienyl | " | 150 |

In mammalian cells, FKBP-12 complexes with the inositol triphosphate receptor ($IP_3R$) and the ryanodine receptor (RyR). It is believed that the neurotrophic compounds of this invention disassociates FKBP-12 from these complexes causing the calcium channel to become "leaky" (Cameron et al., 1995). Calcium fluxes are involved in neurite extensions so that the $IP_3R$ receptor and the ryanodine receptor might be involved in the neurotrophic effects of drugs. Since the drugs bind to the same site as FKBP-12 as the $IP_3R$ receptor, one could assume that the drugs displace the channels from FKBP-12.

Chick Dorsal Root Ganglion Cultures and Neurite Outgrowth

Dorsal root ganglia were dissected from chick embryos of ten day gestation. Whole ganglion explants were cultured on thin layer Matrigel-coated 12 well plates with Liebovitz L15 plus high glucose media supplemented with 2 mM glutamine and 10% fetal calf serum, and also containing 10 $\mu$M cytosine $\beta$-D arabinofuranoside (Ara C) at 37° C. in an environment containing 5% $CO_2$. Twenty-four hours later, the DRGs were treated with various concentrations of nerve growth factor, immunophilin ligands or combinations of NFG plus drugs. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs are cultured per well, and each treatment was performed in duplicate.

The data for these experiments are presented in Table II. Representative photomicrographs for Example 17 are shown in FIG. 1; a dose response curve for this Example is given in FIG. 2.

TABLE II

Neurite Outgrowth in Chick DRG

| Example No. | $ED_{50}$, neurite outgrowth, nM |
|---|---|
| 1 | 53 |
| 2 | 105 |
| 3 | 149 |
| 4 | 190 |
| 5 | 10 |
| 6 | 75 |
| 10 | 0.46 |
| 11 | 0.015 |
| 14 | 2 |
| 15 | 0.8 |
| 16 | 0.015 |
| 17 | 0.05 |
| 18 | 30 |
| 19 | 6 |
| 20 | 0.13 |
| 21 | 0.025 |
| 22 | 0.66 |
| 23 | 1100 |
| 24 | 0.014 |
| 25 | 0.50 |
| 26 | 2 |
| 27 | 500 |
| 28 | 0.50 |
| 29 | 10 |
| 30 | 100 |

Sciatic Nerve Axotomy

Six-week old male Sprague-Dawley rats were anesthetized, and the sciatic nerve exposed and crushed, at the level of the hip, by forceps. Test compounds or vehicle were administered subcutaneously just prior to the lesion and daily for the following 18 days. Sections of the sciatic nerve were stained with Holmes silver stain to quantify the number of axons, and Luxol fast blue to quantify the level of myelination. Eighteen days after lesion, there was a significant decrease in the number of axons (50% decrease as compared to non-lesioned control) and degree of myelination (90% decrease as compared to non-lesioned control) in animal treated with vehicle.

Administration of Example 1 (30 mg/kg s.c.), just prior to the lesion and daily for 18 days following the lesion, resulted in significant regeneration of both axon number (5% decrease as compared to non-lesioned control) and the degree of myelination (50% decrease as compared to control) as compared to vehicle treated animals. The significant efficacy of Example 1 is consistent with its potent activity in inhibiting rotamase activity and stimulating neurite outgrowth in chick DRGs. These results are shown in FIGS. 3A–3D. "Sham" denotes control animals that received vehicle but were not lesioned; "Vehicle" denotes animals that were lesioned and received only vehicle (i.e., no drug). Example 1 showed a striking similarity to the sham treated animals, demonstrating the powerful neuroregenerative effects of these compounds in vivo. "Inactive" is a compound that is inactive as an FKBP12 inhibitor. Animals treated with this compound resembled the vehicle-treated lesioned animals, consistent with the neuroregenerative results observed with Example 1 being directly caused by its inhibition of FKBP12. Quantitation for these data are shown in Table III.

TABLE III

| Treatment | Axon Number (% Control) | Myelin Level |
|---|---|---|
| Sham Lesion: | 100 | 100 |
| + Vehicle (s.c.) | 50 | 10 |
| +Example 1 (30 mg/kg s.c.) | 100 | 50 |
| + Inactive (30 mg/kg s.c.) | 25 | 25 |

MPTP Model of Parkinson's Disease in Mice

MPTP lesioning of dopaminergic neurons in mice was used as an animal model of Parkinson's Disease. Four week old male CD1 white mice were dosed i.p. with 30 mg/kg of MPTP for 5 days. Example 17 (10–40 mg/kg), or vehicle, were administered s.c. along with the MPTP for 5 days, as well as for an additional 5 days following cessation of MPTP treatment. At 18 days following MPTP treatment, the animals were sacrificed and the striata were dissected and homogenized. Binding of [3H]CFT, a radioligand for the dopamine transporter, to the stiatal membranes was done to quantitate the level of the dopamine transporter (DAT) following lesion and drug treatment. Immunostaining was performed on saggital and coronal brain sections using anti-tyrosine hydoxylase Ig to quantitate survival and recovery of dopaminergic neurons. In animals treated with MPTP and vehicle, a substantial loss of functional dopaminergic terminals was observed as compared to non-lesioned animals. Lesioned animals receiving Example 17 showed a nearly quantitative recovery of TH-stained dopaminergic neurons.

FIGS. 4 and 5 show the quantitation in DAT levels, whereas FIGS. 6A–6E, 7A–7E and 8A–8E are photomicrographs showing the regenerative effects of Example 17 in this model. FIG. 4 demonstrates the significant recovery in functional dopaminergic terminals, as assayed by [3H]-CFT binding, relative to animals receiving MPTP but not the Guilford compounds. FIG. 5 gives this data in bar graph form. It is shown that animals receiving 40 mg/kg of Example 17 in addition to MPTP manifested a greater than 90% recovery of [3H]-CFT binding. As shown in FIGS. 6A–6E, 7A–7E and 8A–8E, immunostaining for tyrosine hydroxylase (a marker of viable dopaminergic neurons) in the striatum, the nigra, and the medial forebrain bundle, shows a clear and marked recovery of functional neurons in animals that received Example 17, as compared to animals that received lesioning agent but no drug (MPTP/Vehicle).

The following examples are illustrative of preferred embodiments of the invention and are not to be construed as limiting the invention thereto. All preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

EXAMPLES

The inventive compounds may be prepared by a variety of synthetic sequences that utilize established chemical transformations. The general pathway to the present compounds is described in Scheme I. N-glyoxylproline derivatives may be prepared by reacting L-proline methyl ester with methyl oxalyl chloride as shown in Scheme I. The resulting oxamates may be reacted with a variety of carbon nucleophiles to obtain intermediates compounds. These intermediates are then reacted with a variety of alcohols, amides, or protected amino acid residues to obtain the propyl esters and amides of the invention.

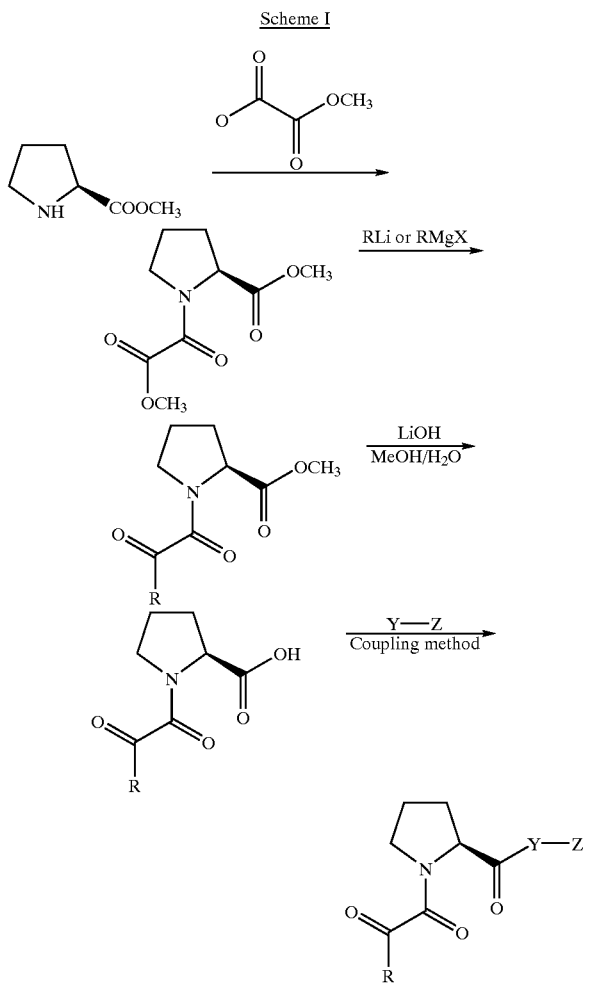

Example 1

Synthesis of 3-phenyl-1-propyl (2S)-1-(3,3-dimethyl-1,2-dioxopentyl)-2-pyrrolidinecarboxylate (Example 1).

Synthesis of methyl (2S)-1-(1,2-dioxo-2-methoxyethyl)-2-pyrrolidinecarboxylate.

A solution of L-proline methyl ester hydrochloride (3.08 g; 18.60 mmol) in dry methylene chloride was cooled to 0° C. and treated with triethylamine (3.91 g; 38.74 mmol; 2.1 eq). After stirring the formed slurry under a nitrogen atmosphere for 15 min, a solution of methyl oxalyl chloride (3.20 g; 36.12 mmol) in methylene chloride (45 mL) was added dropwise. The resulting mixture was stirred at 0° C. for 1.5 hr. After filtering to remove solids, the organic phase was washed with water, dried over $MgSO_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1$H NMR ($CDCl_3$): d 1.93 (dm, 2H); 2.17 (m, 2H); 3.62 (m, 2H); 3.71 (s, 3H); 3.79, 3.84 (s, 3H total); 4.86 (dd, 1H, J=8.4, 3.3).

Synthesis of methyl (2S)-1-(1,2-dioxo-3,3-dimethylpentyl)-2-pyrrolidinecarboxylate.

A solution of methyl (2S)-1-(1,2-dioxo-2-methoxyethyl)-2-pyrrolidinecarboxylate (2.35 g; 10.90 mmol) in 30 mL of tetrahydrofuran (THF) was cooled to −78° C. and treated with 14.2 mL of a 1.0 M solution of 1,1-dimethylpropylmagnesium chloride in THF. After stirring the resulting homogeneous mixture at −78° C. for three hours, the mixture was poured into saturated ammonium chloride (100 mL) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. $^1$H NMR ($CDCl_3$): d 0.88 (t, 3H); 1.22, 1.26 (s, 3H each); 1.75 (dm, 2H); 1.87–2.10 (m, 3H); 2.23 (m, 1H); 3.54 (m, 2H); 3.76 (s, 3H); 4.52 (dm, 1H, J=8.4, 3.4).

Synthesis of (2S)-1-(1,2-dioxo-3,3-dimethylpentyl)-2-pyrrolidinecarboxylic acid.

A mixture of methyl (2S)-1-(1,2-dioxo-3,3-dimethylpentyl)-2-pyrrolidinecarboxylate (2.10 g; 8.23 mmol), 1 N LiOH (15 mL), and methanol (50 mL) was stirred at 0° C. for 30 min and at room temperature overnight. The mixture was acidified to pH 1 with 1 N HCl, diluted with water, and extracted into 100 mL of methylene chloride. The organic extract was washed with brine and concentrated to deliver 1.73 g (87%) of snow-white solid which did not require further purification. $^1$H NMR ($CDCl_3$): d 0.87 (t, 3H); 1.22, 1.25 (s, 3H each); 1.77 (dm, 2H); 2.02 (m, 2H); 2.17 (m, 1H); 2.25 (m, 1H); 3.53 (dd, 2H, J=10.4, 7.3); 4.55 (dd, 1H, J=8.6, 4.1).

Synthesis of 3-phenyl-1-propyl (2S)-1-(3,3-dimethyl-1,2-dioxopentyl)-2-pyrrolidinecarboxylate (Example 1). A mixture of (2S)-1-(1,2-dioxo-3,3-dimethylpentyl)-2-pyrrolidine-carboxylic acid (600 mg; 2.49 mmol), 3-phenyl-1-propanol (508 mg; 3.73 mmol), dicyclohexylcarbodiimide (822 mg; 3.98 mmol), camphorsulphonic acid (190 mg; 0.8 mmol) and 4-dimethylaminopyridine (100 mg; 0.8 mmol) in methylene chloride (20 mL) was stirred overnight under a nitrogen atmosphere. The reaction mixture was filtered through Celite to remove solids and concentrated in vacuo, and the crude material was purified on a flash column (25% ethyl acetate in hexane) to obtain 720 mg (80%) of Example 1 as a colorless oil. $^1$H NMR ($CDCl_3$): d 0.84 (t, 3H); 1.19 (s, 3H); 1.23 (s, 3H); 1.70 (dm, 2H); 1.98 (m, 5H); 2.22 (m, 1H); 2.64 (m, 2H); 3.47 (m, 2H); 4.14 (m, 2H); 4.51 (d, 1H); 7.16 (m, 3H); 7.26 (m, 2H).

The method of Example 1 was utilized to prepare the following illustrative examples:

Example 2

3-phenyl-1-prop-2-(E)-enyl (2S)-1-(3,3-dimethyl-1,2-dioxopentyl)-2-pyrrolidinecarboxylate, 80%, $^1$H NMR (360 Mhz, $CDCl_3$): d 0.86 (t, 3H); 1.21 (s, 3H); 1.25 (s, 3H); 1.54–2.10 (m, 5H); 2.10–2.37 (m, 1H); 3.52–3.55 (m, 2H); 4.56 (dd, 1H, J=3.8, 8.9); 4.78–4.83 (m, 2H); 6.27 (m, 1H); 6.67 (dd, 1H, J=15.9); 7.13–7.50 (m, 5H).

Example 3

3-(3,4,5-trimethoxyphenyl)-1-propyl (2S)-1-(3,3-dimethyl-1,2-dioxopentyl)-2-pyrrolidine-carboxylate, 61%, ¹H NMR (CDCl₃): d 0.84 (t, 3H); 1.15 (s, 3H); 1.24 (s, 3H); 1.71 (dm, 2H); 1.98 (m, 5H); 2.24 (m, 1H); 2.63 (m, 2H); 3.51 (t, 2H); 3.79 (s, 3H); 3.83 (s, 3H); 4.14 (m, 2H); 4.52 (m, 1H); 6.36 (s, 2H).

Example 4

3-(3,4,5-trimethoxyphenyl)-1-prop-2-(E)-enyl (2S)-1-(3,3-dimethyl-1,2-dioxopentyl)-2-pyrrolidine carboxylate, 66% ¹H NMR (CDCl₃): d 0.85 (t, 3H); 1.22 (s, 3H); 1.25 (s, 3H); 1.50–2.11 (m, 5H); 2.11–2.40 (m, 1H); 3.55 (m, 2H); 3.85 (s, 3H); 3.88 (s, 6H); 4.56 (dd, 1H); 4.81 (m, 2H); 6.22 (m, 1H); 6.58 (d, 1H, J=16); 6.63 (s, 2H).

Example 5

3-(4,5-methylenedioxyphenyl)-1-propyl (2S)-1-(3,5-dimethyl-1,2-dioxopentyl)-2-pyrrolidine-carboxylate, 82%, ¹H NMR (360 MHz, CDCl₃): d 0.86 (t, 3H); 1.22 (s, 3H); 1.25 (s, 3H); 1.60–2.10 (m, 5H); 3.36–3.79 (m, 2H); 4.53 (dd, 1H, J=3.8, 8.6); 4.61–4.89 (m, 2H); 5.96 (s, 2H); 6.10 (m, 1H); 6.57 (dd, 1H, J=6.2, 15.8); 6.75 (d, 1H, J=8.0); 6.83 (dd, 1H, J=1.3, 8.0); 6.93 (s, 1H).

Example 6

3-(4,5-methylenedioxyphenyl)-1-prop-2-(E)-enyl (2S)-1-(3,3-dimethyl-1,2-dioxopentyl)-2-pyrrolidinecarboxylate, 82%, ¹H NMR (360 MHz, CDCl₃): d 0.86 (t, 3H); 1.22 (s, 3H); 1.25 (s, 3H); 1.60–2.10 (m, 5H); 2.10–2.39 (m, 1H); 3.36–3.79 (m, 2H); 4.53 (dd, 1H, J=3.8, 8.6); 4.61–4.89 (m, 2H); 5.96 (s, 2H); 6.10 (m, 1H); 6.57 (dd, 1H, J=6.2, 15.8); 6.75 (d, 1H, J=8.0); 6.83 (dd, 1H, J=1.3, 8.0); 6.93 (s, 1H).

Example 8

3-cyclohexyl-1-prop-2-(E)-enyl (2S)-1-(3,3-dimethyl-1,2-dioxopentyl)-2-pyrrolidinecarboxylate, 92%, ¹H NMR (360 MHz, CDCl₃): d 0.86 (t, 3H); 1.13–1.40 (m+2 singlets, 9H total); 1.50–1.87 (m, 8H); 1.87–2.44 (m, 6H); 3.34–3.82 (m, 2H); 4.40–4.76 (m, 3H); 5.35–5.60 (m, 1H); 5.60–5.82 (dd, 1H, J=6.5, 16).

Example 9

(1R)-1,3-Diphenyl-1-propyl (2S)-1-(3,3-dimethyl-1,2-dioxopentyl)-2-pyrrolidinecarboxylate, 90%, ¹H NMR (360 MHz, CDCl₃): d 0.85 (t, 3H); 1.20 (s, 3H); 1.23 (s, 3H); 1.49–2.39 (m, 7H); 2.46–2.86 (m, 2H); 3.25–3.80 (m, 2H); 4.42–4.82 (m, 1H); 5.82 (td, 1H, J=1.8, 6.7); 7.05–7.21 (m, 3H); 7.21–7.46 (m, 7H).

Example 10

3-phenyl-1-propyl (2S)-1-(1,2-dioxo-2-[2-furanyl])ethyl-2-pyrrolidinecarboxylate, 99%, ¹H NMR (300 MHz, CDCl₃): d 1.66–2.41 (m, 6H); 2.72 (t, 2H, J=7.5); 3.75 (m, 2H); 4.21 (m, 2H); 4.61 (m, 1H); 6.58 (m, 1H); 7.16–7.29 (m, 5H); 7.73 (m, 2H).

Example 11

3-phenyl-1-propyl (2S)-1-(1,2-dioxo-2-[2-thienyl])ethyl-2-pyrrolidinecarboxylate, 81%, ¹H NMR (300 MHz, CDCl₃): d 1.88–2.41 (m, 6H); 2.72 (dm, 2H); 3.72 (m, 2H); 4.05 (m, 1H); 4.22 (m, 1H); 4.64 (m, 1H); 7.13–7.29 (m, 6H); 7.75 (dm, 1H); 8.05 (m, 1H).

Example 13

3-phenyl-1-propyl (2S)-1-(1,2-dioxo-2-phenyl)ethyl-2-pyrrolidinecarboxylate, 99%, ¹H NMR (300 MHz, CDCl₃): d 1.97–2.32 (m, 6H); 2.74 (t, 2H, J=7.5); 3.57 (m, 2H); 4.24 (m, 2H); 4.67 (m, 1H); 6.95–7.28 (m, 5H); 7.51–7.64 (m, 3H); 8.03–8.09 (m, 2H).

Example 14

3-(2,5-dimethoxyphenyl)-1-propyl (2S)-1-(3,3-dimethyl-1,2-dioxopentyl)-2-pyrrolidine-carboxylate, 99%, ¹H NMR (300 MHz, CDCl₃): d 0.87 (t, 3H); 1.22 (s, 3H); 1.26 (s, 3H); 1.69 (m, 2H); 1.96 (m, 5H); 2.24 (m, 1H); 2.68 (m, 2H); 3.55 (m, 2H); 3.75 (s, 3H); 3.77 (s, 3H); 4.17 (m, 2H); 4.53 (d, 1H); 6.72 (m, 3H).

Example 15

3-(2,5-dimethoxyphenyl)-1-prop-2-(E)-enyl (2S)-1-(3,3-dimethyl-1,2-dioxopentyl)-2-pyrrolidine-carboxylate, 99%, ¹H NMR (300 MHz, CDCl₃): d 0.87 (t, 3H); 1.22 (s, 3H); 1.26 (s, 3H); 1.67 (m, 2H); 1.78 (m, 1H); 2.07 (m, 2H); 2.26 (m, 1H); 3.52 (m, 2H); 3.78 (s, 3H); 3.80 (s, 3H); 4.54 (m, 1H); 4.81 (m, 2H); 6.29 (dt, 1H, J=15.9); 6.98 (s, 1H).

Example 16

2-(3,4,5-trimethoxyphenyl)-1-ethyl (2S)-1-(3,3-dimethyl-1,2-dioxopentyl)-2-pyrrolidine-carboxylate, 97%, ¹H NMR (300 MHz, CDCl₃): d 0.84 (t, 3H); 1.15 (s, 3H); 1.24 (s, 3H); 1.71 (dm, 2H); 1.98 (m, 5H); 2.24 (m, 1H); 2.63 (m, 2H); 3.51 (t, 2H); 3.79 (s, 3H); 3.83 (s, 3H); 4.14 (m, 2H); 4.52 (m, 1H); 6.36 (s, 2H).

Example 17

3-(3-Pyridyl)-1-propyl (2S)-1-(3,3-dimethyl-1,2-dioxopentyl)-2-pyrrolidinecarboxylate, 80%, ¹H NMR (CDCl₃, 300 MHz): d 0.85 (t, 3H); 1.23, 1.26 (s, 3H each); 1.63–1.89 (m, 2H); 1.90–2.30 (m, 4H); 2.30–2.50 (m, 1H); 2.72 (t, 2H); 3.53 (m, 2H); 4.19 (m, 2H); 4.53 (m, 1H); 7.22 (m, 1H); 7.53 (dd, 1H); 8.45.

Example 18

3-(2-Pyridyl)-1-propyl (2S)-1-(3,3-dimethyl-1,2-dioxopentyl)-2-pyrrolidinecarboxylate, 88%, ¹H NMR (CDCl₃, 300 MHz): d 0.84 (t, 3H); 1.22, 1.27 (s, 3H each); 1.68–2.32 (m, 8H); 2.88 (t, 2H, J=7.5); 3.52 (m, 2H); 4.20 (m, 2H); 4.51 (m, 1H); 7.09–7.19 (m, 2H); 7.59 (m, 1H); 8.53 (d, 1H, J=4.9).

Example 19

3-(4-Pyridyl)-1-propyl (2S)-1-(3,3-dimethyl-1,2-dioxopentyl)-2-pyrrolidinecarboxylate, 91%, ¹H NMR (CDCl₃, 300 MHz): d 6.92–6.80 (m, 4H); 6.28 (m, 1H); 5.25 (d, 1H, J=5.7); 4.12 (m, 1H); 4.08 (s, 3H); 3.79 (s, 3H); 3.30 (m, 2H); 2.33 (m, 1H); 1.85–1.22 (m, 7H); 1.25 (s, 3H); 1.23 (s, 3H); 0.89 (t, 3H, J=7.5).

Example 20

3-phenyl-1-phenyl-1-propyl (2S)-1-(2-cyclohexyl-1,2-dioxoethyl)-2-pyrrolidinecarboxylate, 91%, ¹H NMR (CDCl₃, 300 MHz): d 1.09–1.33 (m, 5H); 1.62–2.33 (m, 12H); 2.69 (t, 2H, J=7.5); 3.15 (dm, 1H); 3.68 (m, 2H); 4.16 (m, 2H); 4.53, 4.84 (d, 1H total); 7.19 (m, 3H); 7.29 (m, 2H).

Example 21

3-phenyl-1-propyl (2S)-1-(2-tert-butyl-1,2-dioxoethyl)-2-pyrrolidinecarboxylate, 92%, ¹H NMR (CDCl₃, 300 MHz): d 1.29 (s, 9H); 1.94–2.03 (m, 5H); 2.21 (m, 1H); 2.69 (m, 2H); 3.50–3.52 (m, 2H); 4.16 (m, 2H); 4.53 (m, 1H); 7.19 (m, 3H); 7.30 (m, 2H).

Example 22

3-phenyl-1-propyl (2S)-1-(2-cyclohexyl-ethyl-1,2-dioxoethyl)-2-pyrrolidinecarboxylate, 97%, $^1$H NMR (CDCl$_3$, 300 MHz): d 0.88 (m, 2H); 1.16 (m, 4H); 1.43–1.51 (m, 2H); 1.67 (m, 5H); 1.94–2.01 (m, 6H); 2.66–2.87 (m, 4H); 3.62–3.77 (m, 2H); 4.15 (m, 2H); 4.86 (m, 1H); 7.17–7.32 (m, 5H).

Example 23

3-(3-pyridyl)-1-propyl (2S)-1-(2-cyclohexylethyl-1,2-dioxoethyl)-2-pyrrolidinecarboxylate, 70%, $^1$H NMR (CDCl$_3$, 300 MHz): d 0.87 (m, 2H); 1.16 (m, 4H); 1.49 (m, 2H); 1.68 (m, 4H); 1.95–2.32 (m, 7H); 2.71 (m, 2H); 2.85 (m, 2H); 3.63–3.78 (m, 2H); 4.19 (m, 2H); 5.30 (m, 1H); 7.23 (m, 1H); 7.53 (m, 1H); 8.46 (m, 2H).

Example 24

3-(3-pyridyl)-1-propyl (2S)-1-(2-tert-butyl-1,2-dioxoethyl)-2-pyrrolidinecarboxylate, 83%, $^1$H NMR (CDCl$_3$, 300 MHz): d 1.29 (s, 9H); 1.95–2.04 (m, 5); 2.31 (m, 1H); 2.72 (t, 2H, J=7.5); 3.52 (m, 2H); 4.18 (m, 2H); 4.52 (m, 1H); 7.19–7.25 (m, 1H); 7.53 (m, 1H); 8.46 (m, 2H).

Example 25

3,3-diphenyl-1-propyl (2S)-1-(3,3-dimethyl-1,2-dioxopentyl)-2-pyrrolidinecarboxylate, 99%, $^1$H NMR (CDCl$_3$, 300 MHz): d 0.85 (t, 3H); 1.21, 1.26 (s, 3H each); 1.68–2.04 (m, 5H); 2.31 (m, 1H); 2.40 (m, 2H); 3.51 (m, 2H); 4.08 (m, 3H); 4.52 (m, 1H); 7.18–7.31 (m, 10H).

Example 26

3-(3-pyridyl)-1-propyl (2S)-1-(2-cyclohexyl-1,2-dioxoethyl)-2-pyrrolidinecarboxylate, 88%, $^1$H NMR (CDCl$_3$, 300 MHz): d 1.24–1.28 (m, 5H); 1.88–2.35 (m, 11H); 2.72 (t, 2H, J=7.5); 3.00–3.33 (dm, 1H); 3.69 (m, 2H); 4.19 (m, 2H); 4.55 (m, 1H); 7.20–7.24 (m, 1H); 7.53 (m, 1H); 8.47 (m, 2H).

Example 27

3-(3-Pyridyl)-1-propyl (2S)-N-([2-thienyl] glyoxyl) pyrrolidinecarboxylate, 49%, $^1$H NMR (CDCl$_3$, 300 MHz): d 1.81–2.39 (m, 6H); 2.72 (dm, 2H); 3.73 (m, 2H); 4.21 (m, 2H); 4.95 (m, 1H); 7.19 (m, 2H); 7.61 (m, 2H); 7.80 (d, 1H); 8.04 (d, 1H); 8.46 (m, 2H).

Example 28

3,3-Diphenyl-1-propyl (2S)-1-(3,3-dimethyl-1,2-dioxobutyl)-2-pyrrolidinecarboxylate, 99%, $^1$H NMR (CDCl$_3$, 300 MHz): d 1.27 (s, 9H); 1.96 (m, 2H); 2.44 (m, 4H); 3.49 (m, 1H); 3.64 (m, 1H); 4.08 (m, 4H); 4.53 (dd, 1H); 7.24 (m, 10H).

Example 29

3,3-Diphenyl-1-propyl (2S)-1-cyclohexyl glyoxyl-2-pyrrolidinecarboxylate, 91%, $^1$H NMR (CDCl$_3$, 300 MHz): d 1.32 (m, 6H); 1.54–2.41 (m, 10H); 3.20 (dm, 1H); 3.69 (m, 2H); 4.12 (m, 4H); 4.52 (d, 1H); 7.28 (m, 10H).

Example 30

3,3-Diphenyl-1-propyl (2S)-1-(2-thienyl) glyoxyl-2-pyrrolidinecarboxylate, 75%, $^1$H NMR (CDCl$_3$, 300 MHz): d 2.04 (m, 3H); 2.26 (m, 2H); 2.48 (m, 1H); 3.70 (m, 2H); 3.82–4.18 (m, 3H total); 4.64 (m, 1H); 7.25 (m, 11H); 7.76 (dd, 1H); 8.03 (m, 1H).

The requisite substituted alcohols may be prepared by a number of methods known to those skilled in the art of organic synthesis. As described in Scheme II, alkyl or aryl aldehydes may be homologated to phenyl propanols by reaction with methyl (triphenylphosphoranylidene) acetate to provide a variety of trans-cinnamates; these latter may be reduced to the saturated alcohols by reaction with excess lithium aluminum hydride, or sequentially by reduction of the double bond by catalytic hydrogenation and reduction of the saturated ester by appropriate reducing agents. Alternatively, the trans-cinnamates may be reduced to (E)-allylic alcohols by the use of diisobutylaluminum hydride.

Scheme II

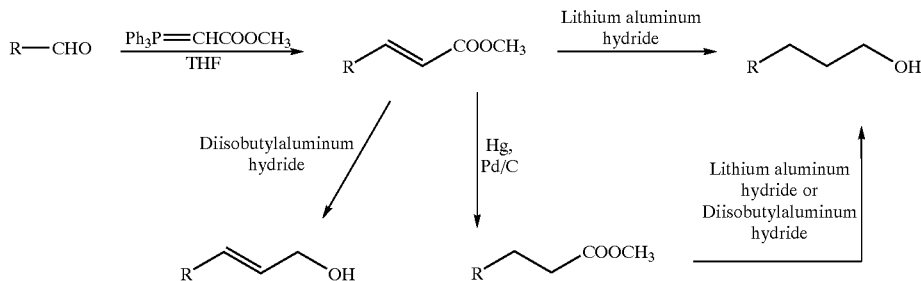

Longer chain alcohols may be prepared by homologation of benzylic and higher aldehydes. Alternatively, these aldehydes may be prepared by conversion of the corresponding phenylacetic and higher acids, and phenethyl and higher alcohols.

General procedure for the synthesis of acrylic esters, exemplified for methyl (3,3,5-trimethoxy)-trans-cinnamate:

A solution of 3,4,5-trimethoxybenzaldehyde (5.0 g; 25.48 mmol) and methyl (triphenyl-phosphoranylidene)acetate (10.0 g; 29.91 mmol) in tetrahydrofuran (250 mL) was refluxed overnight. After cooling, the reaction mixture was diluted with 200 mL of ethyl acetate and washed with 2×200 mL of water, dried, and concentrated in vacuo. The crude residue was chromatographed on a silica gel column, eluting with 25% ethyl acetate in hexane, to obtain 5.63 g (86%) of the cinnamate as a white crystalline solid, $^1$H NMR (300 Mhz; CDCl$_3$): d 3.76 (s, 3H); 3.85 (s, 6H); 6.32 (d, 1H, J=16); 6.72 (s, 2H); 7.59 (d, 1H, J=16).

General procedure for the synthesis of saturated alcohols from acrylic esters. Exemplified for (3,4,5-trimethoxy) phenylpropanol.

A solution of methyl (3,3,5-trimethoxy)-trans-cinnamate (1.81 g; 7.17 mmol) in tetrahydrofuran (30 mL) was added in a dropwise manner to a solution of lithium aluminum hydride (14 mmol) in THF (35 mL), with stirring and under an argon atmosphere. After the addition was complete, the mixture was heated to 75° C. for 4 hours. After cooling, it was quenched by the careful addition of 15 mL of 2N NaOH followed by 50 mL of water. The resulting mixture was filtered through Celite to remove solids, and the filter cake was washed with ethyl acetate. The combined organic fractions were washed with water, dried, concentrated in vacuo, and purified on a silica gel column, eluting with ethyl acetate to obtain 0.86 g (53%) of the alcohol as a clear oil, $^1$H NMR (300 Mhz; CDCl$_3$): d 1.23 (br, 1H); 1.87 (m, 2H); 2.61 (t, 2H, J=7.1); 3.66 (t, 2H); 3.80 (s, 3H); 3.83 (s, 6H); 6.40 (s, 2H).

General procedure for the synthesis of trans-allylic alcohols from acrylic esters. Exemplified for (3,4,5-trimethoxy)phenylprop-2-(E)-enol.

A solution of methyl (3,3,5-trimethoxy)-trans-cinnamate (1.35 g; 5.35 mmol) in toluene (25 mL) was cooled to −10° C. and treated with a solution of diisobutylaluminum hydride in toluene (11.25 mL of a 1.0 M solution; 11.25 mmol). The reaction mixture was stirred for 3 hrs at 0° C. and then quenched with 3 mL of methanol followed by 1 N HCl until the pH was 1. The reaction mixture was extracted into ethyl acetate and the organic phase was washed with water, dried and concentrated. Purification on a silica gel column eluting with 25% ethyl acetate in hexane furnished 0.96 g (80%) of a thick oil, $^1$H NMR (360 Mhz; CDCl$_3$): d 3.85 (s, 3H); 3.87 (s, 6H); 4.32 (d, 2H, J=5.6); 6.29 (dt, 1H, J=15.8, 5.7); 6.54 (d, 1H, J=15.8); 6.61 (s, 2H).

The invention being thus described, it will be obvious that the same may be varied in many ways. Such variations are not to be regarded as a departure from the spirit and scope of the invention and all such modification are intended to be included within the scope of the following claims.

What is claimed is:

1. A process for preparing a compound having the formula:

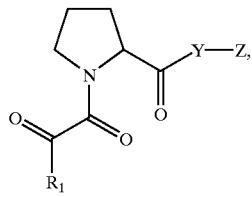

comprising reacting compound A having the formula:

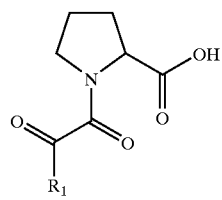

with a compound having the formula:
Y–Z
wherein:
$R_1$ represents
  a $C_1$–$C_9$ straight or branched chain alkyl or alkenyl group optionally substituted with $C_3$–$C_8$ cycloalkyl,
  $C_3$ or $C_5$ cycloalkyl,
  $C_5$–$C_7$ cycloalkenyl,
  where said alkyl, alkenyl, cycloalkyl, or cycloalkenyl groups may be optionally substituted with $C_1$–$C_4$ alkyl, $C_1$–$C_4$ alkenyl, or hydroxy, or $Ar_1$, where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-, 3-, or 4-pyridyl, and phenyl, having one to three substituents which are independently selected from the group consisting of hydrogen, halogen, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino;

Y is HO or $HNR_2$, where $R_2$ is hydrogen or $C_1$–$C_6$ alkyl; and

Z is a $C_2$–$C_6$ straight or branched chain alkyl or alkenyl, wherein the alkyl chain is substituted in one or more positions with $Ar_1$ as defined above, $C_3$–$C_8$ cycloalkyl, cycloalkyl connected by a $C_1$–$C_6$ straight or unbranched alkyl or alkenyl chain, or $Ar_2$ where $Ar_2$ is selected from the group consisting of 2-indolyl, 3-indolyl, 2-furyl, 3-furyl, 2-thiazolyl, 2-thienyl, 3-thienyl, 2-, 3-, or 4-pyridyl, and phenyl, having one to three substituents which are independently selected from the group consisting of hydrogen, halogen, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino.

2. The process of claim 1, further comprising the step of contacting the compound of formula

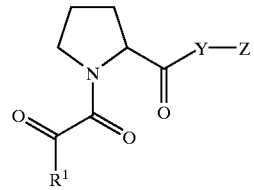

with an effective amount of an inorganic or organic acid or base to form a pharmaceutically acceptable salt.

3. The process of claim 1, wherein compound A is prepared by hydrolyzing a compound having the formula:

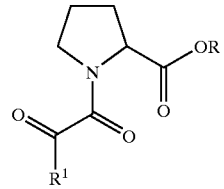

wherein $R_1$ is as defined in claim 1 and R is a $C_2$–$C_6$ straight or branched chain alkyl or alkenyl, wherein the alkyl chain is substituted in one or more positions with $Ar_1$, $C_3$–$C_8$ cycloalkyl, cycloalkyl connected by a $C_1$–$C_6$ straight or unbranched alkyl or alkenyl chain, or $Ar_2$, having one to three substituents which are independently selected from the group consisting of hydrogen, halogen, hydroxyl, nitro, trifluoromethyl, $C_1$–$C_6$ straight or branched alkyl or alkenyl, $C_1$–$C_4$ alkoxy or $C_1$–$C_4$ alkenyloxy, phenoxy, benzyloxy, and amino.

4. The process of claim 3, further comprising the step of contacting the compound of formula

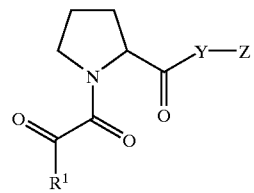

with an effective amount of an inorganic or organic acid or base to form a pharmaceutically acceptable salt.

* * * * *

UNITED STATES PATENT AND TRADEMARK OFFICE
CERTIFICATE OF CORRECTION

PATENT NO. : 6,500,959 B1
DATED : December 31, 2002
INVENTOR(S) : Gregory S. Hamilton and Joseph P. Steiner It is certified that error appears in the above-identified patent and that said Letters Patent is hereby corrected as shown below:

Column 23,
Line 57, please delete "Y-Z" and insert -- HY-Z --.

Column 24,
Line 10, please delete "HO or $HNR_2$" and insert -- oxygen or $NR_2$ --.

Signed and Sealed this

Fourteenth Day of December, 2004

JON W. DUDAS
*Director of the United States Patent and Trademark Office*